US010420850B2

(12) United States Patent
Leamon

(10) Patent No.: US 10,420,850 B2
(45) Date of Patent: Sep. 24, 2019

(54) METHOD OF IMAGING WITH A CHELATING AGENT

(71) Applicant: ENDOCYTE, INC., West Lafayette, IN (US)

(72) Inventor: Christopher Paul Leamon, West Lafayette, IN (US)

(73) Assignee: Endocyte, Inc., West Lafayette, IN (US)

( * ) Notice: Subject to any disclaimer, the term of this patent is extended or adjusted under 35 U.S.C. 154(b) by 58 days.

(21) Appl. No.: 15/751,299

(22) PCT Filed: Aug. 11, 2016

(86) PCT No.: PCT/US2016/046527
§ 371 (c)(1),
(2) Date: Feb. 8, 2018

(87) PCT Pub. No.: WO2017/030893
PCT Pub. Date: Feb. 23, 2017

(65) Prior Publication Data
US 2019/0111162 A1  Apr. 18, 2019

Related U.S. Application Data

(60) Provisional application No. 62/205,621, filed on Aug. 14, 2015.

(51) Int. Cl.
A61K 51/00 (2006.01)
A61M 36/14 (2006.01)
A61K 51/04 (2006.01)

(52) U.S. Cl.
CPC ...... A61K 51/0478 (2013.01); A61K 51/0497 (2013.01)

(58) Field of Classification Search
CPC .... A61K 51/00; A61K 51/0478; A61K 51/04; A61K 51/0497; A61K 51/088; A61K 51/08; A61K 38/00; A61K 2121/00; A61K 2123/00; A61K 51/0459; A61K 51/0402; A61K 51/025; A61K 51/02; A61K 51/48107; A61K 47/48; A61K 47/48023
USPC .... 424/1.11, 1.65, 1.69, 9.1, 9.2; 514/1, 1.1, 514/19.2, 19.3, 19.4, 19.5, 19.6; 530/300; 534/7, 10–16
See application file for complete search history.

(56) References Cited

U.S. PATENT DOCUMENTS

| 2,816,110 | A | 12/1957 | Sletzinger et al. |
| 4,879,303 | A | 11/1989 | Davison et al. |
| 5,053,493 | A | 10/1991 | Pak et al. |
| 5,140,104 | A | 8/1992 | Coughlin et al. |
| 5,175,343 | A | 12/1992 | Fritzberg et al. |
| 5,242,679 | A | 9/1993 | Fritzberg et al. |
| 5,552,545 | A | 9/1996 | Pearce et al. |
| 5,688,488 | A | 11/1997 | Low et al. |
| 6,221,334 | B1 | 4/2001 | Wedeking et al. |
| 6,335,434 | B1 | 1/2002 | Guzaev et al. |
| 7,128,893 | B2* | 10/2006 | Leamon ............ A61K 51/0459 424/9.1 |
| 7,740,854 | B2 | 6/2010 | Low et al. |
| 7,862,798 | B2* | 1/2011 | Leamon ............ A61K 51/0459 424/1.11 |
| 8,313,728 | B2* | 11/2012 | Leamon ............ A61K 51/0459 424/1.11 |
| 8,834,842 | B2* | 9/2014 | Leamon ............ A61K 51/0459 424/1.11 |
| 2002/0001782 | A1 | 1/2002 | Watanabe et al. |
| 2002/0192157 | A1 | 12/2002 | Low et al. |
| 2004/0033195 | A1 | 2/2004 | Leamon et al. |
| 2007/0031334 | A1 | 2/2007 | Leamon et al. |
| 2009/0324499 | A1 | 12/2009 | Leamon et al. |
| 2010/0324008 | A1 | 12/2010 | Low et al. |
| 2013/0237687 | A1 | 9/2013 | Leamon et al. |
| 2014/0065068 | A1* | 3/2014 | Leamon ............ A61K 51/0459 424/1.69 |

FOREIGN PATENT DOCUMENTS

| CA | 2445826 | 11/2002 |
| EP | 0220030 | 10/1986 |
| EP | 0273085 | 12/1986 |
| JP | 2774378 | 2/1998 |
| WO | WO 92/13572 | 2/1992 |
| WO | WO 1995/15335 | 6/1995 |
| WO | WO 1998/49196 | 11/1998 |
| WO | WO 2000/73332 A1 | 12/2000 |
| WO | WO 2001/091807 | 12/2001 |
| WO | WO 2002/087424 | 11/2002 |
| WO | WO 2003/092742 | 11/2003 |
| WO | WO 2004/069159 | 8/2004 |

(Continued)

OTHER PUBLICATIONS

Leamon, Christopher P. et al., "Synthesis and Biological Evaluation of EC20: A New Folate Derived, $^{99m}$tc-Based Radiopharmaceutical", Bioconjugate Chem., vol. 13, No. 6, Nov.-Dec. 2002, pp. 1200-1210 (XP-002353910).

Yang, D. J. et al. "Imaging-Tumor Folate Receptors Using Radiolabeled Folate and Methotrexate", Journal of Labelled Compounds and Radiopharmaceuticals, Sussex, GB, vol. Suppl. 1, No. 42, Jun. 1999, pp. S696-S697 (XP-001073918).

Ilgan, S. et al., "Imaging Tumor Folate Receptors Using 111IN-DTPA-Methotrexate," Cancer Biother. Radiopharm., 13(3): 177 (1998).

Hosomi, Akihiro et al., "Affinity for A-Tocopherol Transfer Protein as a Determinant of the Biological Activities of Vitamen E Analogs," Journal Article, Federation of European Biochemical Societies, 1997, vol. 409. pp. 105-108.

(Continued)

Primary Examiner — D. L. Jones
(74) Attorney, Agent, or Firm — Barnes & Thornburg, LLP

(57) ABSTRACT

The present disclosure relates to a method for imaging cancer by administering to a patient a labeled chelating compound and an unlabeled chelating compound.

24 Claims, 5 Drawing Sheets

(56) References Cited

FOREIGN PATENT DOCUMENTS

| WO | WO 2004/100983 | 11/2004 |
|---|---|---|
| WO | WO 2011/106639 | 9/2011 |

OTHER PUBLICATIONS

Shimizu, Kazui et al., "Novel Vitamin D3 Antipsoriatic Antedrugs: 16-En-22-Oxa-1a,25-(OH)2D3 Analogs," Bioorganic & Medicinal Chemistry 14, 2006, pp. 1838-1850.
Takasu, Hisashi et al., "C-Fos Protein as a Target of Anti-Osteoclastogenic Action of Vitamin D, and Synthesis of New Analogs," Journal Article, The Journal of Clinical Investigation, vol. 116, No. 2, Feb. 2006, pp. 528-535.
Shimizu, Masato et al., "Synthesis and Biological Activities of New 1a,25-Dihydroxy-19-Norvitamin D3 Analogs With Modifications in Both the A-Ring and the Side Chain," Journal Article, Biorganic & Medicinal Chemistry, 2006, Eighteen Pages.
Agoston, E. S. et al., "Vitamin D Analogs as Anti Carcinogenic Agents," Journal Article, Anti-Cancer Agents in Medicinal Chemistry, 2006, pp. 53-71.
Westerhof, G. Robbin et al., "Carrier- and Receptor-Mediated Transport of Folate Antagonists Targeting Folate-Dependent Enzymes: Correlates of Molecular-Structure and Biological Activity," Journal Article, Molecular Pharmacology, 1995, vol. No. 48, pp. 459-471.
Roberts, Eugene C. et al., "Folic Acid Analogs. Modifications in the Benzene-Ring Region. 3. Neohomofolic and Neobishomofolic Acids. An Improved Synthesis of Folic Acid and Its Analogs", Journal Article, Journal of Medicinal Chemistry, 1973, vol. 16, No. 6, pp. 697-699.
Roberts, Eugene C. et al., "Folic Acid Analogs. Modifications in the Benzene-Ring Region. 2. Thiazole Analogs," Journal Article, Journal of Medicinal Chemistry, 1972, vol. 15, No. 12, pp. 1310-1312.
Roberts, Eugene C. et al., "Folic Acid Analogs. Modifications in the Benzene-Ring Region. 1. 2'- and 3'-Azafolic Acids," Journal Article, Journal of Medicinal Chemistry, 1971, vol. 14, No. 2, pp. 125-130.
Weinstock, Louis T. et al., "Folic Acid Analogs. II. P-{[2,6-Diamino-8-Purinyl)Methyl]Amino}-Benzoyl-L-Glutamic Acid and Related Compounds," Journal Article, Journal of Medicinal Chemistry, 1970, vol. 13, No. 5, pp. 995-997.
Bock, Lothar et al., "Sulfonamide Structure-Activity Relationships in a Cell-Free System. 2. Proof for the Formation of a Sulfonamide-Containing Folate Analog.," Journal Article, Journal of Medicinal Chemistry, 1974, vol. 17, No. 1, pp. 23-28.
Roberts, Eugene C. et al., Folic Acid Analogs. Modifications in the Benzene-Ring Region. 4. 3'-Ethyl - and 3'-Isopropylfolic Acids, Journal Article, Journal of Medicinal Chemistry, 1974, vol. 17, No. 2, pp. 219-222.
Lee, William W. et al., "Folic Acid Antagonists. Methotrexate Analogs Containing Spurious Amino Acids. Dichlorohomofolic Acid.", Journal Article, Journal of Medicinal Chemistry, 1974, vol. 17, No. 3, pp. 326-330.
Kim, Y. H. et al., "Synthesis and Biological Activity of 10-Thia-10-Deaza Analogs of Folic Acid, Pteroic Acid, and Related Compounds," Journal Article, Journal of Medicinal Chemistry, 1975, vol. 18, No. 8, pp. 776-780.
Nair, M. G. et al., "Folate Analogues Altered in the C9-N10 Bridge Region. 10-Oxafolic Acid and 10-Oxaaminopterin," Journal Article, Journal of Medicinal Chemistry, 1976, vol. 19, No. 6, pp. 825-829.
Plante, Laurence T. et al., "Polyglutamyl and Polylysyl Derivatives of the Lysine Analogues of Folic Acid and Homofolic Acid," Journal Article, Journal of Medicinal Chemistry, 1976, vol. 19, No. 11, pp. 1295-1299.
Hynes, John B. et al., "Quinazolines as Inhibitors of Dihydrofolate Reductase. 4. Classical Analogues of Folic and Isofolic Acids," Journal Article, Journal of Medicinal Chemistry, 1977, vol. 20, No. 4, pp. 588-591.
Oatis Jr., John E. et al., "Synthesis of Quinazoline Analogues of Folic Acid Modified at Position 10," Journal Article, Journal of Medicinal Chemistry, 1977, vol. 20, No. 11, pp. 1393-1396.

Nair, M. G. et al., "Folate Analogues Altered in the C9-N10 Bridge Region: N10-Tosylisohomofolic Acid and N10-Tosylisohomoaminopterin," Journal Article, Journal of Medicinal Chemistry, 1978, vol. 21, No. 7, pp. 673-677.
Nair, M. G. et al., "Folate Analogues Altered in the C9-N10 Bridge Region: 11-Thiohomofolic Acid," Journal Article, Journal of Medicinal Chemistry, 1979, vol. 22, No. 7, pp. 850-855.
Nair, M. G. et al., "Folate Analogues Altered in the C9-N10 Bridge Region. 14. 11-Oxahomofolic Acid, A Potential Antitumor Agent," Journal Article, J. Med. Chem., 1980, vol. 23, pp. 59-65.
Nair, M. G. et al., "Folate Analogues Altered in the C9-N10 Bridge Region. 18. Synthesis and Antitumor Evaluation of 11-Oxahomoaminopterin and Related Compounds," Journal Article, J. Med. Chem., 1981, vol. 24, pp. 1068-1073.
Temple, Jr., Carroll et al., "Synthesis of Pseudo Cofactor Analogues as Potential Inhibitors of the Folate Enzymes," Journal Article, J. Med. Chem., 1982, vol. 25, pp. 161-166.
Nair, M. G. et al., "Folate Analogues. 20. Synthesis and Antifolate Activity of 1, 2, 3, 4, 5, 6,-Hexahydrohomofolic Acid," Journal Article, J. Med. Chem., 1983, vol. 26, pp. 135-140.
Nair, M. G. et al., "Folate Analogues. 21. Synthesis and Antifolate and Antitumor Activities of N10-(Cyanomethyl)-5,8-Dideazafolic Acid," Journal Article, J. Med. Chem., 1983, vol. 26, pp. 605-607.
Nair, M. G. et al., "Folate Analogues. 22. Synthesis and Biological Evaluation of Two Analogues of Dihydrofolic Acid Processing a 7,8-Dihydro-8-Oxapterin Ring System," Journal Article, J. Med. Chem., 1983, vol. 26, pp. 1164-1168.
Lonsdale, Derrick "A Review of the Biochemistry, Metabolism and Clinical Benefits of Thiamin(E) and Its Derivatives," Publication, Advance Access Publication, vol. 3, Feb. 2006, pp. 49-59, 1988.
Nosaka, K. et al., "Separate Determination of Anticoccidial Thiamine Analogs by High-Performance Liquid Chromatography," Journal Article, Actaa Vitaminol. Et Enzymol, 1984, vol. 6 (2), pp. 137-142.
Kandiko, Charles T. et al., "Inhibition of Rat Brain Pyruvate Dehydrogenase by Thiamine Analogs," Journal Article, Biochemical Pharmacology, vol. 37, No. 22, pp. 4375-4380, 1988.
Spry, Christina et al., "A Class of Pantothenic Acid Analogs Inhibits Plasmodium Falciparum Pantothenate Kinase and Represses the Proliferation of Malaria Parasites," Journal Article, Antimicrobial Agents and Chemotherapy, Nov. 2005, pp. 4649-4657.
Sargent, Dale R. et al., "Antimetabolites of Pantothenic Acid, Ureido- and Carbamoyl-Derivatives," Journal Article, Texas Reports on Biology and Medicine, 1975, vol. 33, No. 3, pp. 433-443.
Abstract, Acta Vitaminol Enzymol, 1982, vol. 4 (1-2), pp. 87-97.
Kagechika, Hiroyuki et al., "Synthetic Retinoids: Recent Developments Concerning Structure and Clinical Utility," Journal Article, Journal of Medicinal Chemistry, Sep. 22, 2005, vol. 48, No. 19, pp. 5875-5883.
Shealy, Y. Fulmer "Synthesis and Evaluation of Some New Retinoids for Cancer Chemoprevention," Preventive Medicine, 1989, vol. 18, pp. 624-645.
Landuer, Walter et al., "The Interaction in Teratogenic Activity of the Two Niacin Analogs 3-Acetylpyridine and 6-Aminonicotinamide," Storrs Agricultural Experiment Station, University of Connecticut, Undated, pp. 253-258.
Renz, Paul et al., "Synthesis of 4-Aza-5, 6-Diethylbenzimidazole and Biosynthetic Preparation of 4- and 7-Aza-5, 6-Dimethylbenzimidazolylcobamide," Journal Article, Z. Naturforsch, 1997, vol. 52c, pp. 287-291. V.
Ayers, William A. "Effect of Vitamin B12 and Analogs on the Respiration of a Marine Bacterium," Journal Article, Archives of Biochemistry and Biophysics, vol. 96, 1962, pp. 210-215.
Toraya, Tetsuo et al., "Immobilized Derivatives of Vitamin B12 Coenzyme and Its Analogs," Journal Article, Methods in Enzymology, vol. 67, pp. 57-66.
Ueda, Masatoshi et al., "Effect of Vitamin B12 Derivatives on Urinary Excretion of Methylmalonic Acid in Liver Diseases," Journal Article, Acta Med. Okayama, 1970, vol. 24, pp. 365-372.
Toraya, Tetsuo et al., "The Synthesis of Several Immobilized Derivatives of Vitamin B12 Coenzyme and Their Use as Affinity Adsorbents for a Study of Interactions of Diol Dehydrase With the

(56) References Cited

OTHER PUBLICATIONS

Coenzyme," The Journal of Biological Chemistry, vol. 255, No. 8., Issue of Apr. 25, 1980, pp. 3520-3525.
Takahata, Yusuke et al., Synthesis, Properties and Microbiological Activity of Hydrophobic Derivatives of Vitamin B12, Journal Article, J. Nutr. Sci. Vitaminol., vol. 41, 1995, pp. 515-526.
Kamao, Maya et al., "Determination of Plasma Vitamin K by High Performance Liquid Chromatography With Fluorescence Detection Using Vitamin K Analogs as Internal Standards," Journal Article, Journal of Chromatography B, vol. 816, 2005, pp. 41-48.
Nishikawa, Yuji et al., "Growth Inhibition of Hepatoma Cells Induced by Vitamin K and Its Analogs," Journal Article, The Journal of Biological Chemistry, vol. 270, No. 47, Issue of Nov. 24, 1995, pp. 28304-28310.
Mack, Donald O. et al., "The Carboxylation Activity of Vitamin K Analogs With Substitutions at Position 2, 3, or 5," The Journal of Biological Chemistry, vol. 254, Issue of Apr. 25, 1979, pp. 2656-2664.
Mock, Donald M. et al., "Urinary Biotin Analogs Increase in Humans During Chronic Supplementation: The Analogs Are Biotin Metabolites," The American Physiological Society, 1997, pp. 83-85.
Shoup, Timothy M. et al., "Synthesis of Fluorine-18-Labeled Biotin Derivatives: Biodistribution and Infection Localization," Journal Article, J. Nucl. Med. 1994, vol. 35, pp. 1685-1690.
Vesely, David L. et al., "Biotin Analogs Activate Guan Ylate Cyclase," Journal Article, Molecular and Cellular Biochemistry, vol. 60, 1984, pp. 109-114.
Lambooy, J. P. "Riboflavin Analogs Utilized for Metabolism by a Lactobacillus Casei Mutant," Int. J. Biochem., vol. 16, No. 2, 1984, pp. 231-234.
Nielsen, Peter et al., "Phosphates of Riboflavin and Riboflavin Analogs: A Reinvestigation by High-Performance Liquid Chromatography," Journal Article, Analytical Biochemistry, vol. 130, 1983, pp. 359-368.
Arya, P. et al., "Design and Synthesis of Analogs of Vitamin E: Antiproliferative Activity Against Human Breast Adenocarcinoma Cells," Journal Article, Bioorganic & Medicinal Chemistry Letters, vol. 8, 1998, pp. 2433-2438.
Trachewsky, Daniel "Antihypertensive Effect of Riboflavin Analogs in Rats With Mineralocorticoid-Induced Hypertension," Journal Article, Hypertension, vol. 3, No. 1, Jan.-Feb. 1981, pp. 75-80.
Skinner, W.A. et al., "Structure-Activity Relations in the Vitamin E Series. II. Derivatives of A-Tocopherol Substituted at the 5-Methyl Group," Journal Article, Skinner, Parkhurst, Scholler, and Schwarz, vol. 12, pp. 64-66.
Neuzil, J. et al., "Vitamin E Analogs: A New Class of Multiple Action Agents With Anti-Neoplastic and Anti-Atherogenic Activity," Apoptosis, vol. 7, 2002, pp. 179-187.
Politis, I. et al., "The Effect of Various Vitamin E Derivatives on the Urokinase-Plasminogen Activator System of Ovine Macrophages and Neutrophils," British Journal of Nutrition, vol. 89, 2003, pp. 259-265.
Wang, Fang-Xiu et al., "Vitamin E Analogs Trigger Apoptosis in HER2/erbB2-Overexpressing Breast Cancer Cells by Signaling Via the Mitochondrial Pathway," Biochemical and Biophysical Research Communication, vol. 326, 2005, pp. 282-289.
Leamon C.P. et al., "Folate-mediated drug delivery: effect of alternative conjugation chemistry," *Journal of Drug Targeting*, 1999; 7(3):157-169.
Leamon C.P. et al., "Folate-liposome-mediated antisense oligodeoxynucleotide targeting to cancer cells: evaluation in vitro and in vivo," *Bioconjugate Chem.*, 2003; 14:738-747.
Ilgan, S., et al., "$^{99m}$Tc-Ethylenedicysteine-Folate: A New Tumor Imaging Agent. Syntheis, Labeling and Evaluation in Animals," Cancer Biotherapy & Radiopharmaceuticals, 1998, vol. 13(6), 427-435.
Gafiteanu E. et al., "Oral lypohilizate—an alternative for products with low-soluble drugs", Rev Med Chir Soc Med Nat Iasi., 101 (3-4), pp. 170-173, 1997 (Abstract).
Berge S. M. et al., "Pharmaceutical Salts", Journal of Pharmaceutical Sciences, 46/1, pp. 2-16, 1977 (Abstract).
International Search Report for PCT Application No. PCT/US2016/012653.
European search report for EP 16837542.6 dated Feb. 19, 2019.
Maurer et al., "Imaging the Folate Receptor on Cancer Cells with 99mTc-Etarfolatide: Properties, Clinical Use, and Future Potential of Folate Receptor Imaging", J Nucl Med 2014; 55:701-704.
PCT Search Report and Written Opinion for PCT/US2016/046527, completed Sep. 28, 2016.

\* cited by examiner

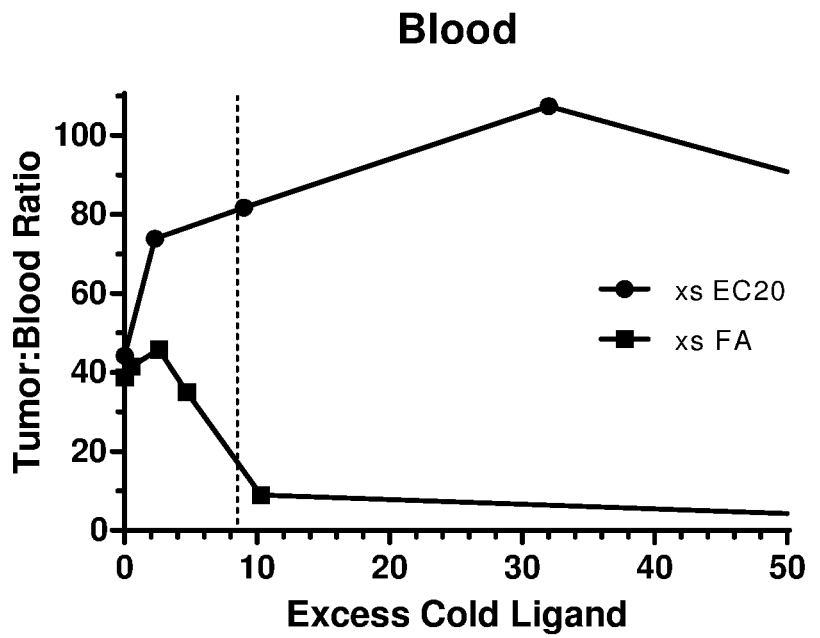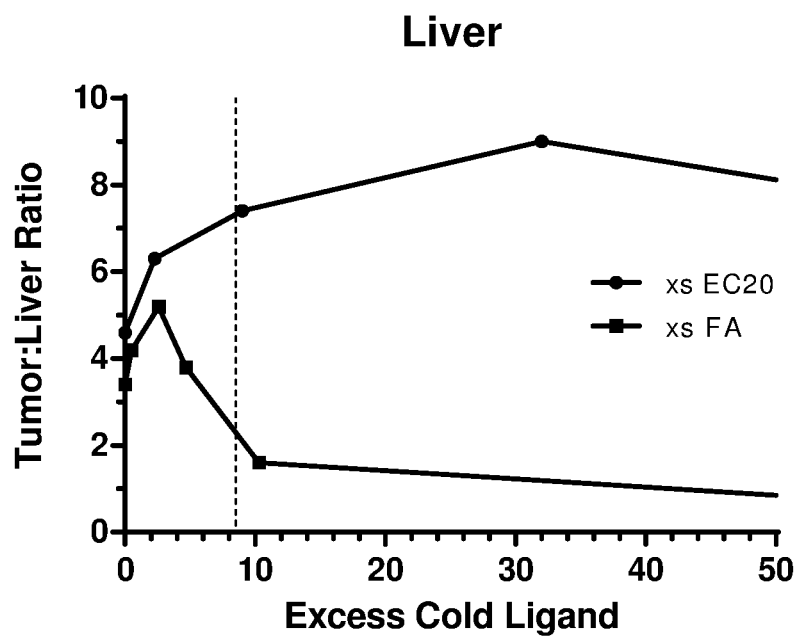
FIGURE 1
Continued on Another Page

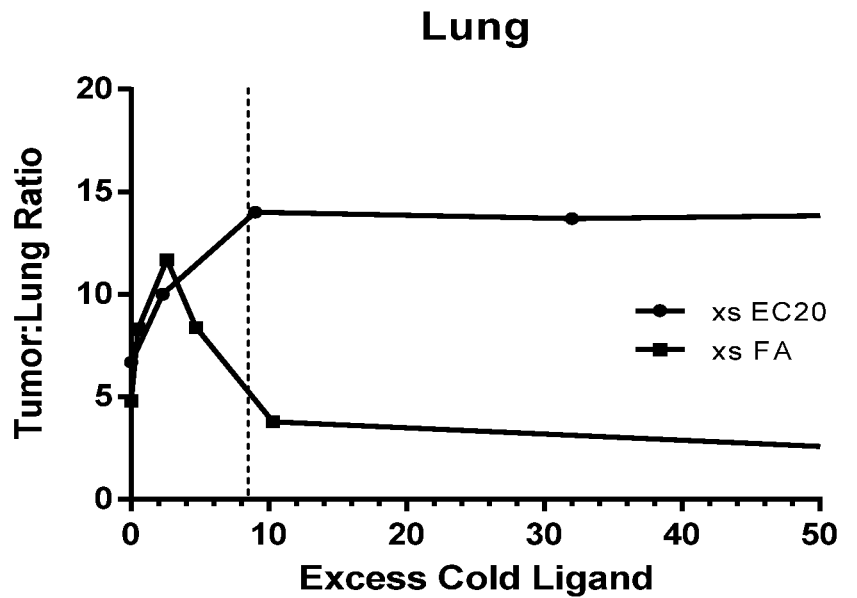
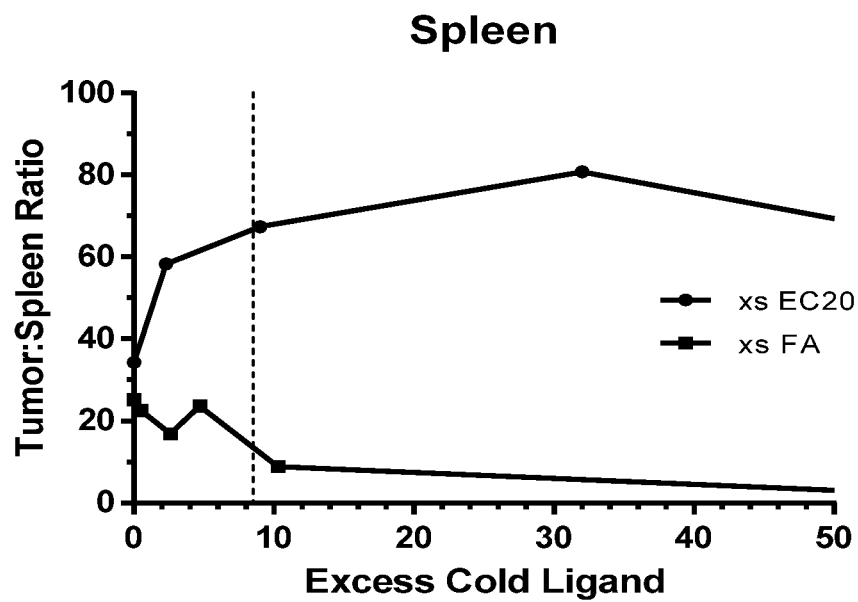
FIGURE 1
Continued on Another Page

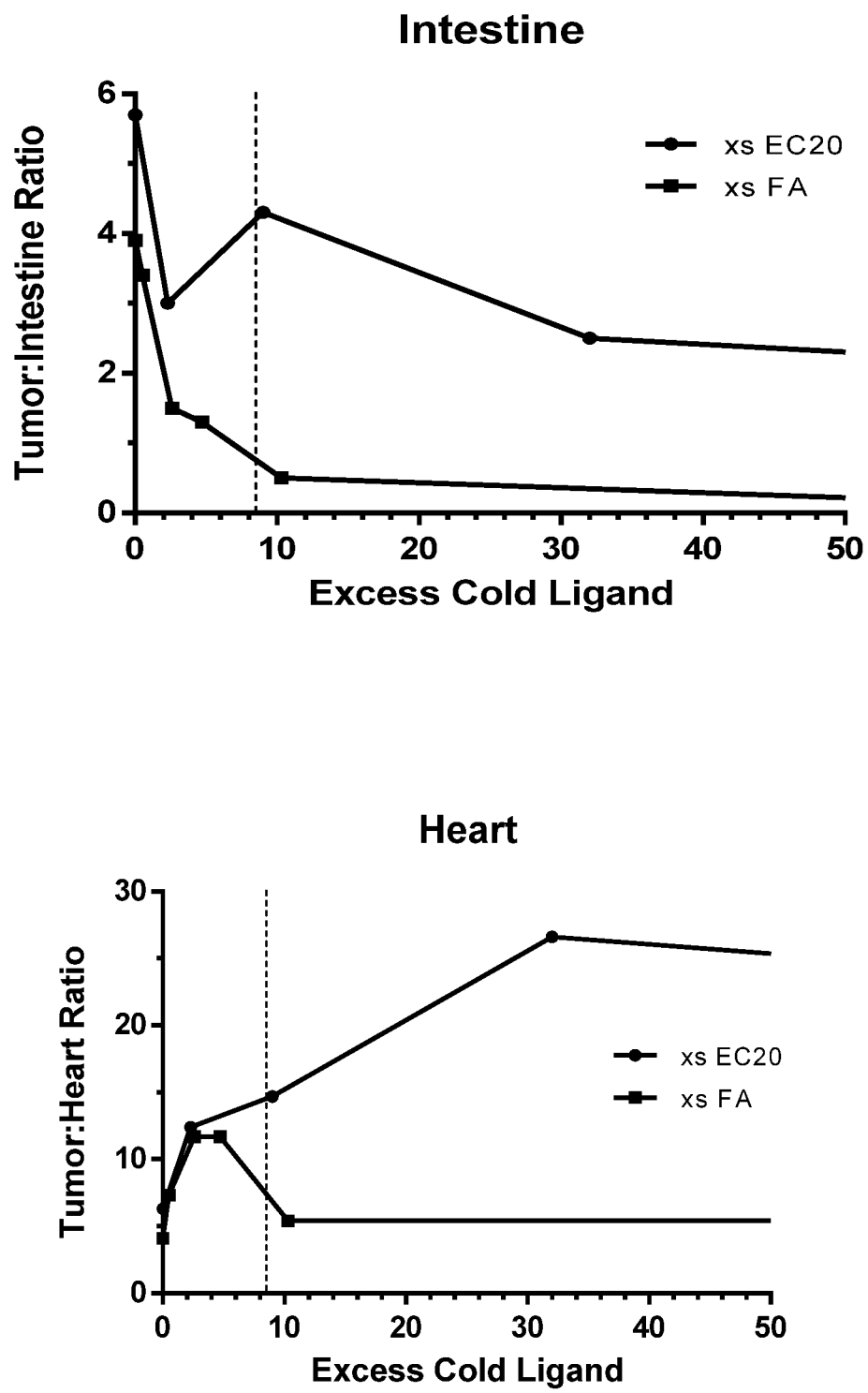
FIGURE 1
Continued on Another Page

METHOD OF IMAGING WITH A CHELATING AGENT

CROSS REFERENCE TO RELATED APPLICATIONS

This application is a U.S. national stage application under 35 U.S.C. § 371(b) of International Application No. PCT/US2016/046527 filed Aug. 11, 2016, which claims priority under 35 U.S.C. § 119(e) to U.S. Provisional Application Ser. No. 62/205,621, filed Aug. 14, 2015, both of which are incorporated herein by reference in their entirety.

TECHNICAL FIELD

The present disclosure relates to the field of imaging, for example, to a method of imaging using a labeled chelating compound and an unlabeled chelating compound.

BACKGROUND

The folate receptor (FR) is a glycoprotein that is over-expressed in many types of cancer cells and inflammatory cells, but is minimally distributed in normal tissues. For example, folate receptors are over-expressed in a number of human epithelial cancers, including cancer of the ovary, lung, brain (primary and metastatic), endometrium, and kidney, and inflammatory cells of the immune system, such as macrophages and monocytes. Whereas folic acid enters most normal cells via the reduced folate carrier, it is known that the folate receptor, via receptor mediated endocytosis, is capable of internalizing folate conjugates, thus offering a route to target cancerous cells or inflammatory cells, for example.

Folate-targeted technology may be clinically useful, in that folate-linked imaging agents can be used to identify folate receptor (FR) expression on cancer cells, for example. For cancers, FR expression has traditionally been determined through immunohistochemical (IHC) analysis of archived tissue specimens derived at the time of the primary resection/histologic characterization of the cancer. Since FR expression may change during the course of the disease, IHC analysis may be conducted on tissue that is not temporally related to the current state of FR expression in patients. PET, MRI and SPECT/CT imaging techniques can image tissue in almost real-time without the invasiveness of biopsies, and non-invasive folate-targeted imaging agents are important advancements in the field.

SUMMARY OF THE INVENTION

The invention relates to an imaging method using a labeled chelating compound and an unlabeled chelating compound. In one embodiment, a method of imaging a cancer is provided. The method comprises administering to a patient an unlabeled compound according to Formula I

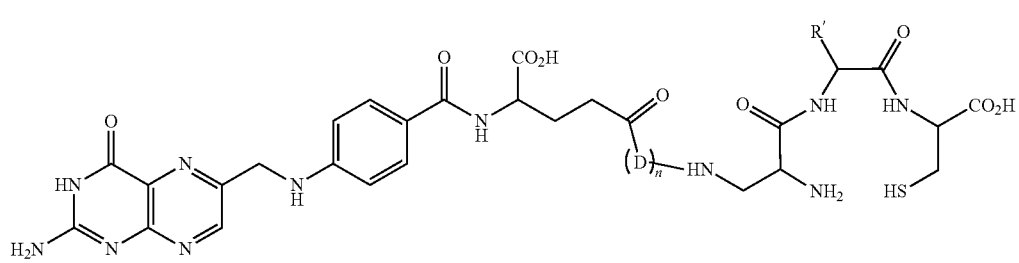

or a pharmaceutically acceptable salt thereof, wherein R' is hydrogen, or R' is selected from the group consisting of alkyl, aminoalkyl, carboxyalkyl, hydroxyalkyl, heteroalkyl, aryl, arylalkyl and heteroarylalkyl, each of which is optionally substituted, wherein D is a divalent linker, and wherein n is 0 or 1, and administering to the patient a labeled compound according to Formula II

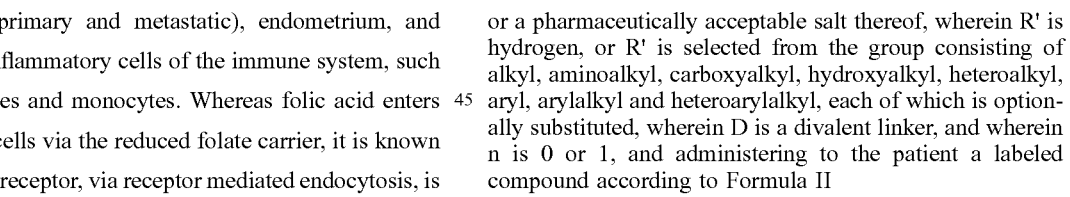

or a pharmaceutically acceptable salt thereof, wherein R' is hydrogen, or R' is selected from the group consisting of alkyl, aminoalkyl, carboxyalkyl, hydroxyalkyl, heteroalkyl, aryl, arylalkyl and heteroarylalkyl, each of which is optionally substituted, wherein D is a divalent linker, wherein n is 0 or 1, and wherein M is a cation of a radionuclide.

Several embodiments are also described by the following enumerated clauses:

1. A method of imaging a cancer, the method comprising administering to a patient an unlabeled compound according to Formula I

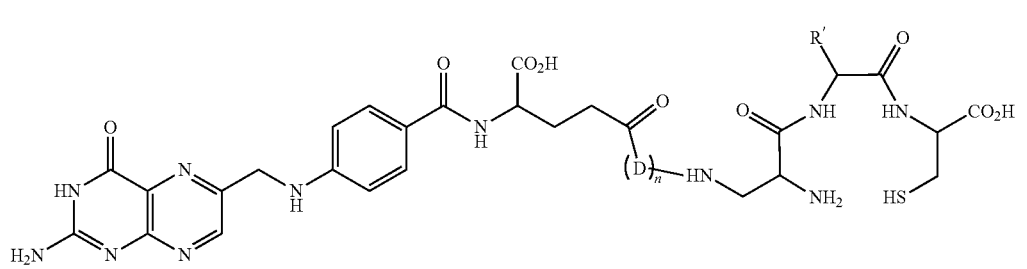

I or a pharmaceutically acceptable salt thereof, wherein R' is hydrogen, or R' is selected from the group consisting of alkyl, aminoalkyl, carboxyalkyl, hydroxyalkyl, heteroalkyl, aryl, arylalkyl and heteroarylalkyl, each of which is optionally substituted, wherein D is a divalent linker, and wherein n is 0 or 1, and administering to the patient a labeled compound according to Formula II

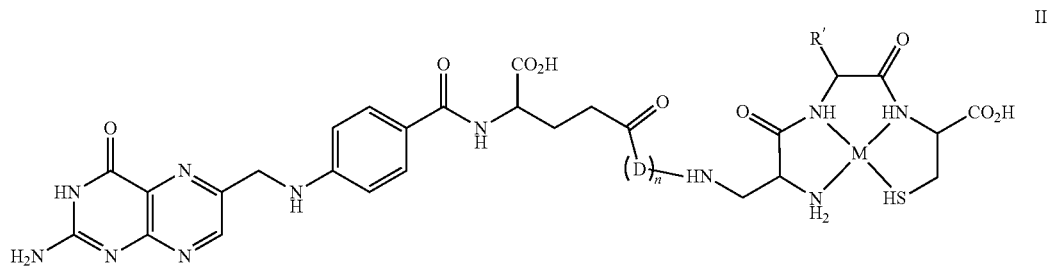

II or a pharmaceutically acceptable salt thereof, wherein R' is hydrogen, or R' is selected from the group consisting of alkyl, aminoalkyl, carboxyalkyl, hydroxyalkyl, heteroalkyl, aryl, arylalkyl and heteroarylalkyl, each of which is optionally substituted, wherein D is a divalent linker, wherein n is 0 or 1, and wherein M is a cation of a radionuclide.

2. The method of clause 1, wherein the unlabeled compound is of the formula

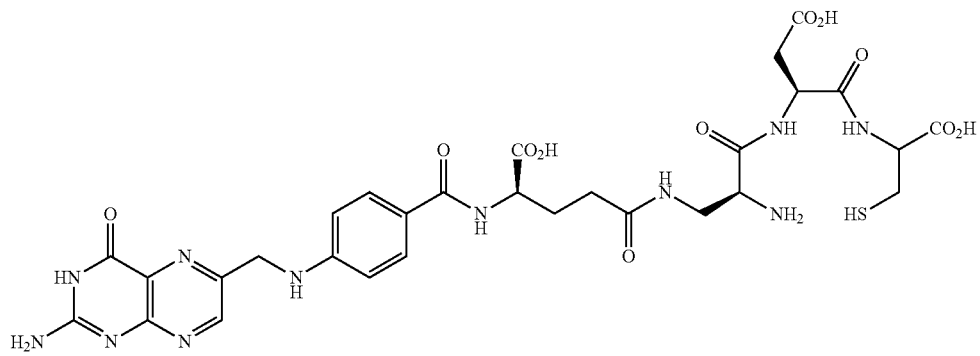 [SMILES: Nc1nc2ncc(CNc3ccc(C(=O)N[C@H](CCC(=O)NC[C@H](N)C(=O)N[C@@H](CC(=O)O)C(=O)NC(CS)C(=O)O)C(=O)O)cc3)nc2c(=O)[nH]1]

or a pharmaceutically acceptable salt thereof, and the labeled compound is of the formula

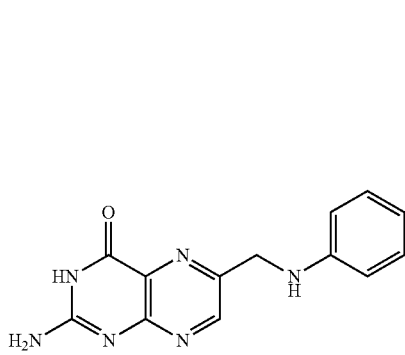

or a pharmaceutically acceptable salt thereof, and wherein M is a cation of a radionuclide.

3. The method of any of the preceding clauses wherein the patient is administered the unlabeled compound, or a pharmaceutically acceptable salt thereof, before the patient is administered the labeled compound, or a pharmaceutically acceptable salt thereof.

4. The method of any of the preceding clauses, wherein the cancer is selected from the group consisting of lung cancer, bone cancer, pancreatic cancer, skin cancer, cancer of the head, cancer of the neck, cutaneous melanoma, intraocular melanoma uterine cancer, ovarian cancer, endometrial cancer, rectal cancer, stomach cancer, colon cancer, breast cancer, triple negative breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, non-small cell lung cancer, cancer of the adrenal gland, sarcoma of soft tissue, cancer of the urethra, prostate cancer, chronic leukemia, acute leukemia, lymphocytic lymphoma, pleural mesothelioma, cancer of the bladder, Burkitt's lymphoma, cancer of the ureter, cancer of the kidney, renal cell carcinoma, carcinoma of the renal pelvis, neoplasms of the central nervous system (CNS), primary CNS lymphoma, spinal axis tumors, brain stem glioma, pituitary adenoma, and adenocarcinoma of the gastroesophageal junction.

5. The method of any of the preceding clauses wherein the cancer being imaged is a tumor.

6. The method of any of the preceding clauses wherein the cancer is malignant.

7. The method of any of the preceding clauses wherein the cancer is a folate receptor expressing cancer.

8. The method of any of the preceding clauses wherein the cancer is an endometrial cancer.

9. The method of any of clauses 1-7 wherein the cancer is a non-small cell lung cancer.

10. The method of any of clauses 1-7 wherein the cancer is an ovarian cancer.

11. The method of any of clauses 1-7 wherein the cancer is a triple negative breast cancer.

12. The method of any of the preceding clauses wherein the radionuclide is selected from the group consisting of an isotope of gallium, an isotope of indium, an isotope of copper, an isotope of technetium, and an isotope of rhenium.

13. The method of any of clauses 1-12 wherein the radionuclide is an isotope of gallium.

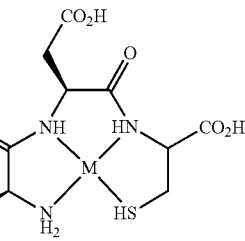

14. The method of any of clauses 1-12 wherein the radionuclide is an isotope of indium.

15. The method of any of clauses 1-12 wherein the radionuclide is an isotope of copper.

16. The method of any of clauses 1-12 wherein the radionuclide is an isotope of technetium.

17. The method of any of clauses 1-12 wherein the radionuclide is an isotope of rhenium.

18. The method of any of the preceding clauses wherein the cancer is imaged about 0.5 hours to about 8 hours after administration of the labeled compound, or a pharmaceutically acceptable salt thereof.

19. The method of any of clauses 1-17 wherein the cancer is imaged about 0.5 hours to about 6 hours after administration of the labeled compound, or a pharmaceutically acceptable salt thereof.

20. The method of any of clauses 1-17 wherein the cancer is imaged about 0.5 hours to about 4 hours after administration of the labeled compound, or a pharmaceutically acceptable salt thereof.

21. The method of any of clauses 1-17 wherein the cancer is imaged about 1 hour to about 3 hours after administration of the labeled compound, or a pharmaceutically acceptable salt thereof.

22. The method of any of clauses 1-21 wherein the patient is administered about a 2-fold to about a 1000-fold excess of the unlabeled compound, or a pharmaceutically acceptable salt thereof, relative to the labeled compound, or pharmaceutically acceptable salt thereof.

23. The method of any of clauses 1-21 wherein the patient is administered about a 2-fold to about a 100-fold excess of the unlabeled compound, or a pharmaceutically acceptable salt thereof, relative to the labeled compound, or pharmaceutically acceptable salt thereof.

24. The method of any of clauses 1-21 wherein the patient is administered about a 2-fold to about a 30-fold excess of the unlabeled compound, or a pharmaceutically acceptable salt thereof, relative to the labeled compound, or pharmaceutically acceptable salt thereof.

25. The method of any of clauses 1-21 wherein the patient is administered about a 2-fold to about a 10-fold excess of the unlabeled compound, or a pharmaceutically acceptable salt thereof, relative to the labeled compound, or pharmaceutically acceptable salt thereof.

26. The method of any of clauses 1-21 wherein the patient is administered about 0.1 mg to about 20 mg of the unlabeled compound, or a pharmaceutically acceptable salt thereof, and the patient is administered about 0.01 mg to about 2 mg of the labeled compound, or a pharmaceutically acceptable salt thereof.

27. The method of any of clauses 1-21 wherein the patient is administered about 0.3 mg to about 10 mg of the unlabeled compound, or a pharmaceutically acceptable salt thereof, and the patient is administered about 0.05 mg to about 0.5 mg of the labeled compound, or a pharmaceutically acceptable salt thereof.

28. The method of any of clauses 1-21 wherein the patient is administered a mass dose of about 50 nmol/kg to about 3000 nmol/kg of patient body weight of the unlabeled compound, or a pharmaceutically acceptable salt thereof, and the labeled compound, or a pharmaceutically acceptable salt thereof.

29. The method of any of clauses 1-21 wherein the patient is administered a mass dose of about 50 nmol/kg to about 500 nmol/kg of patient body weight of the unlabeled compound, or a pharmaceutically acceptable salt thereof, and the labeled compound, or a pharmaceutically acceptable salt thereof.

30. The method of any of clauses 1-21 wherein the patient is administered a mass dose of about 50 nmol/kg to about 400 nmol/kg of patient body weight of the unlabeled compound, or a pharmaceutically acceptable salt thereof, and the labeled compound, or a pharmaceutically acceptable salt thereof.

31. The method of any of clauses 1-21 wherein the patient is administered a mass dose of about 100 nmol/kg to about 300 nmol/kg of patient body weight of the unlabeled compound, or a pharmaceutically acceptable salt thereof, and the labeled compound, or a pharmaceutically acceptable salt thereof.

32. The method of any of clauses 1-21 wherein the patient is administered a mass dose of about 100 nmol/kg of patient body weight of the unlabeled compound, or a pharmaceutically acceptable salt thereof, and the labeled compound, or a pharmaceutically acceptable salt thereof.

33. The method of any of the preceding clauses wherein the patient is administered the unlabeled compound or a pharmaceutically acceptable salt thereof, over a period of about 15 seconds to about 2 minutes.

34. The method of any of the preceding clauses wherein the patient is administered the unlabeled compound, or a pharmaceutically acceptable salt thereof, over a period of about 30 seconds to about 90 seconds.

35. The method of any of the preceding clauses wherein the patient is administered the labeled compound, or a pharmaceutically acceptable salt thereof, over a period of about 15 seconds to about 2 minutes.

36. The method of any of the preceding clauses wherein the patient is administered the unlabeled compound, or a pharmaceutically acceptable salt thereof, about 30 seconds to about 5 minutes before the patient is administered the labeled compound, or a pharmaceutically acceptable salt thereof.

37. The method of any of the preceding clauses wherein the patient is administered the unlabeled compound, or a pharmaceutically acceptable salt thereof, about 1 minute to about 2 minutes before the patient is administered the labeled compound, or a pharmaceutically acceptable salt thereof.

38. The method of any of the preceding clauses wherein the patient is administered saline after the patient is administered the labeled compound, or a pharmaceutically acceptable salt thereof.

39. The method of any of the preceding clauses wherein the cancer is imaged by PET imaging.

40. The method of any of clauses 1-38 wherein the cancer is imaged by MRI imaging.

41. The method of any of clauses 1-38 wherein the cancer is imaged by SPECT/CT imaging.

42. The method of any of the preceding clauses further comprising the step of measuring an amount of radioactivity of the cancer and an amount of radioactivity of a control tissue.

43. The method clause 42 wherein the control tissue is selected from the group consisting of blood, liver, lung, spleen, intestine, heart, kidney, and muscle.

44. The method of clause 42 or clause 43 wherein the amount of radioactivity of the cancer is compared to the amount of radioactivity of aortic arch blood.

45. The method of clause 42 or clause 43 wherein the amount of radioactivity of the cancer is compared to the amount of radioactivity of muscle.

46. The method of clause 42 or clause 43 wherein the amount of radioactivity of the cancer is compared to the amount of radioactivity of lung.

47. The method of clause 42 or clause 43 wherein the amount of radioactivity of the cancer is compared to the amount of radioactivity of the kidney.

48. The method of any of clauses 42-47 further comprising the step of calculating a tumor to background ratio as a quotient of the amount of radioactivity of the cancer compared to the amount of radioactivity of the control tissue.

49. The method of clause 48 wherein the tumor to background ratio is greater than about 2.

50. The method of clause 48 wherein the tumor to background ratio is about 2 to about 150.

51. The method of any of the preceding clauses wherein the labeled compound comprises about 20 mCi to about 25 mCi of technetium-99m.

52. The method of any of the preceding clauses wherein the patient has not taken a folic acid supplement within about 3 weeks of the administration of the labeled compound.

53. The method of any of the preceding clauses wherein the imaged cancer is visually assessed.

54. The method of any of the preceding clauses wherein multiple doses of the unlabeled compound, or a pharmaceutically acceptable salt thereof, and the labeled compound, or a pharmaceutically acceptable salt thereof, are administered.

55. The method of any of the preceding clauses wherein the labeled compound, or a pharmaceutically acceptable salt thereof, is administered to the patient, the unlabeled compound, or a pharmaceutically acceptable salt thereof, is then administered to the patient, and the labeled compound, or a pharmaceutically acceptable salt thereof, is administered to the patient a second time after the unlabeled compound, or a pharmaceutically acceptable salt thereof, is administered to the patient.

56. The method of clause 55 wherein the labeled compound, or a pharmaceutically acceptable salt thereof, is first administered to the patient on day 1 and the unlabeled compound, or a pharmaceutically acceptable salt thereof, and the labeled compound, or a pharmaceutically acceptable salt thereof, are then administered to the patient on day 4 to day 10.

57. The method of clause 55 wherein the labeled compound, or a pharmaceutically acceptable salt thereof, is first administered to the patient on day 1 and the unlabeled compound, or a pharmaceutically acceptable salt thereof, and the labeled compound, or a pharmaceutically acceptable salt thereof, are then administered to the patient on day 5 to day 8.

58. The method of any of clauses 55 to 57 wherein the patient is administered about 0.3 mg to about 10 mg of the unlabeled compound, or a pharmaceutically acceptable salt thereof, and the patient is administered about 0.05 mg to about 0.5 mg of the labeled compound, or a pharmaceutically acceptable salt thereof, each time the labeled compound, or a pharmaceutically acceptable salt thereof, is administered to the patient.

59. The method of any of clauses 55 to 58 wherein the patient is imaged after each administration of the labeled compound, or a pharmaceutically acceptable salt thereof.

60. The method of clause 48, wherein the tumor to background ratio is at least 4.

61. The method of clause 48, wherein the tumor to background ratio is at least 5.

66. The method of clause 48, wherein the tumor to background ratio is at least 10.

67. The method of clause 48, wherein the tumor to background ratio is at least 15.

68. The method of clause 48, wherein the tumor to background ratio is at least 20.

69. The method of clause 48, wherein the tumor to background ratio is at least 25.

70. The method of clause 48, wherein the tumor to background ratio is at between about 2 and about 10.

71. The method of clause 48, wherein the tumor to background ratio is at between about 2 and about 5.

72. The method of clause 48, wherein the tumor to background ratio is at between about 2 and about 4.

DEFINITIONS

Figure 1:
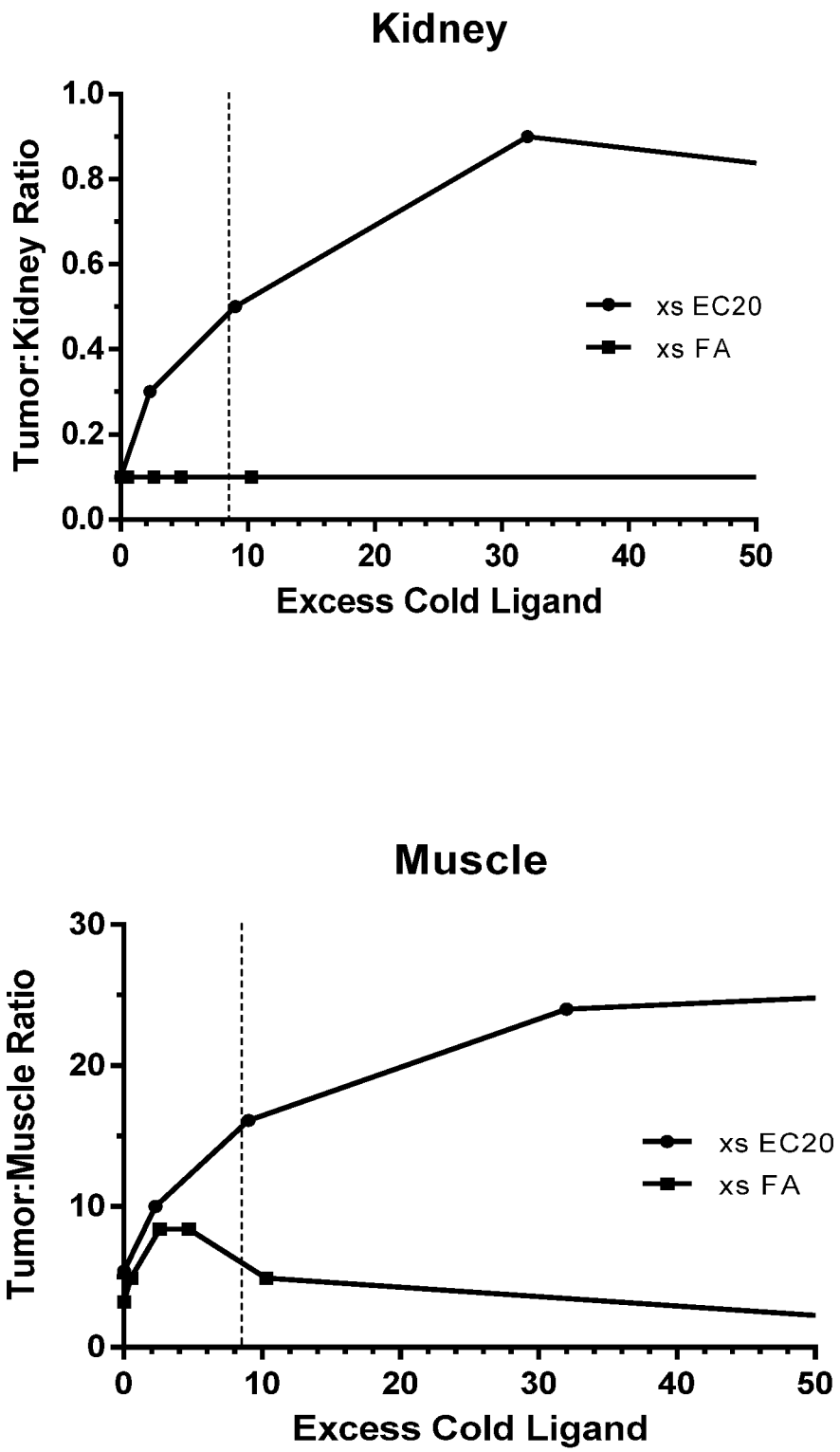
FIG. 1 shows the mass dose effect of unlabeled etarfolatide versus folic acid on $^{99m}$Tc-etarfolatide uptake based on tumor to background (T:NT) ratios.
Figure 2:
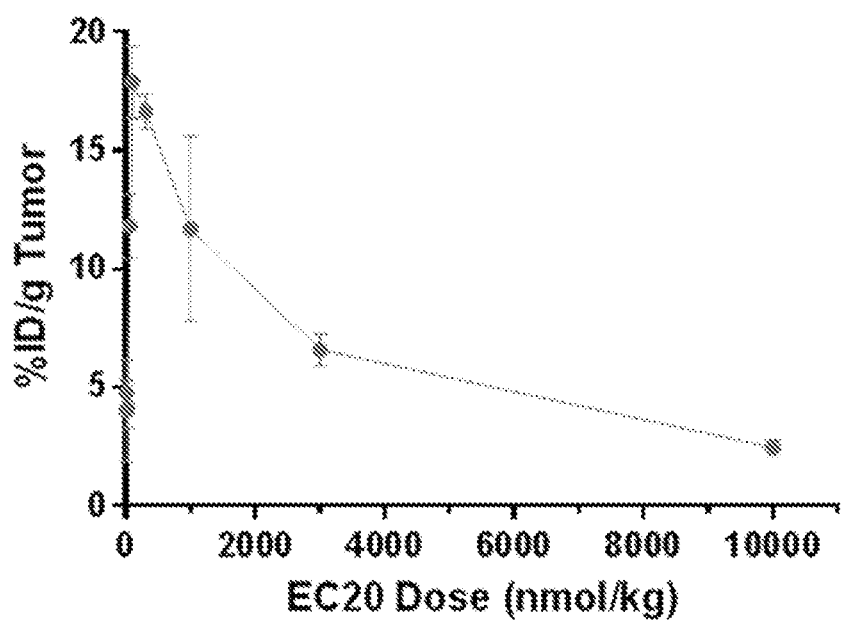
FIG. 2 shows the effect of increasing mass dose of unlabeled etarfolatide and $^{99m}$Tc-etarfolatide on M109 tumor uptake of $^{99m}$Tc-etarfolatide.

As used herein, the term "alkyl" includes a chain of carbon atoms, which is optionally branched and contains from 1 to 20 carbon atoms. It is to be further understood that in certain embodiments, alkyl may be advantageously of limited length, including $C_1$-$C_{12}$, $C_1$-$C_{10}$, $C_1$-$C_9$, $C_1$-$C_8$, $C_1$-$C_7$, $C_1$-$C_6$, and $C_1$-$C_4$. Illustratively, such particularly limited length alkyl groups, including $C_1$-$C_8$, $C_1$-$C_7$, $C_1$-$C_6$, and $C_1$-$C_4$, and the like may be referred to as "lower alkyl." Illustrative alkyl groups include, but are not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl, and the like. Alkyl may be substituted or unsubstituted. Typical substituent groups include cycloalkyl, aryl, heteroaryl, heteroalicyclic, hydroxy, alkoxy, aryloxy, mercapto, alkylthio, arylthio, cyano, halo, carbonyl, oxo, (=O), thiocarbonyl, O-carbamyl, N-carbamyl, O-thiocarbamyl, N-thiocarbamyl, C-amido, N-amido, C-carboxy, O-carboxy, nitro, and amino, or as described in the various embodiments provided herein. It will be understood that "alkyl" may be combined with other groups, such as those provided above, to form a functionalized alkyl. By way of example, the combination of an "alkyl" group, as described herein, with a "carboxy" group may be referred to as a "carboxyalkyl" group. Other non-limiting examples include hydroxyalkyl, aminoalkyl, heteroalkyl, arylalkyl, heteroarylalkyl and the like.

As used herein, the term "aryl" refers to an all-carbon monocyclic or fused-ring polycyclic groups of 6 to 12 carbon atoms having a completely conjugated pi-electron system. It will be understood that in certain embodiments, aryl may be advantageously of limited size such as $C_6$-$C_{10}$ aryl. Illustrative aryl groups include, but are not limited to, phenyl, naphthalenyl and anthracenyl. The aryl group may be unsubstituted, or substituted as described for alkyl or as described in the various embodiments provided herein.

As used herein, the term "heteroaryl" refers to a monocyclic or fused ring group of 5 to 12 ring atoms containing one, two, three or four ring heteroatoms selected from nitrogen, oxygen and sulfur, the remaining ring atoms being carbon atoms, and also having a completely conjugated pi-electron system. It will be understood that in certain embodiments, heteroaryl may be advantageously of limited size such as 3- to 7-membered heteroaryl, 5- to 7-membered heteroaryl, and the like. Heteroaryl may be unsubstituted, or substituted as described for alkyl or as described in the various embodiments provided herein. Illustrative heteroaryl groups include, but are not limited to, pyrrolyl, furanyl, thiophenyl, imidazolyl, oxazolyl, thiazolyl, pyrazolyl, pyridinyl, pyrimidinyl, quinolinyl, isoquinolinyl, purinyl, tetrazolyl, triazinyl, pyrazinyl, tetrazinyl, quinazolinyl, quinoxalinyl, thienyl, isoxazolyl, isothiazolyl, oxadiazolyl, thiadiazolyl, triazolyl, benzimidazolyl, benzoxazolyl, benzthiazolyl, benzisoxazolyl, benzisothiazolyl and carbazoloyl, and the like.

As used herein, "hydroxy" or "hydroxyl" refers to an —OH group.

As used herein, "alkoxy" refers to both an —O-(alkyl) or an —O-(unsubstituted cycloalkyl) group. Representative examples include, but are not limited to, methoxy, ethoxy, propoxy, butoxy, cyclopropyloxy, cyclobutyloxy, cyclopentyloxy, cyclohexyloxy, and the like.

As used herein, "aryloxy" refers to an —O-aryl or an —O-heteroaryl group. Representative examples include, but are not limited to, phenoxy, pyridinyloxy, furanyloxy, thienyloxy, pyrimidinyloxy, pyrazinyloxy, and the like, and the like.

As used herein, "mercapto," or "thiol" refers to an —SH group.

As used herein, "alkylthio" refers to an —S-(alkyl) or an —S-(unsubstituted cycloalkyl) group. Representative examples include, but are not limited to, methylthio, ethylthio, propylthio, butylthio, cyclopropylthio, cyclobutylthio, cyclopentylthio, cyclohexylthio, and the like.

As used herein, "arylthio" refers to an —S-aryl or an —S-heteroaryl group. Representative examples include, but are not limited to, phenylthio, pyridinylthio, furanylthio, thienylthio, pyrimidinylthio, and the like.

As used herein, "halo" or "halogen" refers to fluorine, chlorine, bromine or iodine.

As used herein, "cyano" refers to a —CN group.

As used herein, "O-carbamyl" refers to a —OC(O)NR"R" group, where R" is any R group as described in the various embodiments provided herein.

As used herein, "N-carbamyl" refers to an R"OC(O)NR"— group, where R" is any R group as described in the various embodiments provided herein.

As used herein, "O-thiocarbamyl" refers to a —OC(S)NR"R" group, where R" is any R group as described in the various embodiments provided herein.

As used herein, "N-thiocarbamyl" refers to a R"OC(S)NR"— group, where R" is any R group as described in the various embodiments provided herein.

As used herein, "amino" refers to an —NR"R" group, where R" is any R group as described in the various embodiments provided herein.

As used herein, "C-amido" refers to a —C(O)NR"R" group, where R" is any R group as described in the various embodiments provided herein.

As used herein, "N-amido" refers to a R"C(O)NR"— group, where R" is any R group as described in the various embodiments provided herein.

As used herein, "bond" refers to a covalent bond.

As used herein, "amino acid" means any molecule that includes an alpha-carbon atom covalently bonded to an amino group and an acid group. The acid group may include a carboxyl group. "Amino acid" may include molecules having one of the formulas:

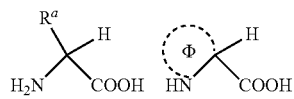

wherein $R^a$ is a side group and $\Phi$ includes at least 3 carbon atoms. "Amino acid" includes stereoisomers such as the D-amino acid and L-amino acid forms. Illustrative amino acid groups include, but are not limited to, the twenty endogenous human amino acids and their derivatives, such as lysine (Lys), asparagine (Asn), threonine (Thr), serine (Ser), isoleucine (Ile), methionine (Met), proline (Pro), histidine (His), glutamine (Gln), arginine (Arg), glycine (Gly), aspartic acid (Asp), glutamic acid (Glu), alanine (Ala), valine (Val), phenylalanine (Phe), leucine (Leu), tyrosine (Tyr), cysteine (Cys), tryptophan (Trp), phosphoserine (PSER), sulfo-cysteine, arginosuccinic acid (ASA), hydroxyproline, phosphoethanolamine (PEA), sarcosine (SARC), taurine (TAU), carnosine (CARN), citrulline (CIT), anserine (ANS), 1,3-methyl-histidine (ME-HIS), alpha-amino-adipic acid (AAA), beta-alanine (BALA), ethanolamine (ETN), gamma-amino-butyric acid (GABA), beta-amino-isobutyric acid (BAIA), alpha-amino-butyric acid (BABA), L-allo-cystathionine (cystathionine-A; CYSTA-A), L-cystathionine (cystathionine-B; CYSTA-B), cystine, allo-isoleucine (ALLO-ILE), DL-hydroxylysine (hydroxylysine (I)), DL-allo-hydroxylysine (hydroxylysine (2)), ornithine (ORN), homocystine (HCY), and derivatives thereof. It will be appreciated that each of these examples are also contemplated in connection with the present disclosure in the D-configuration as noted above. Specifically, for example, D-lysine (D-Lys), D-asparagine (D-Asn), D-threonine (D-Thr), D-serine (D-Ser), D-isoleucine (D-Ile), D-methionine (D-Met), D-proline (D-Pro), D-histidine (D-His), D-glutamine (D-Gln), D-arginine (D-Arg), D-glycine (D-Gly), D-aspartic acid (D-Asp), D-glutamic acid (D-Glu), D-alanine (D-Ala), D-valine (D-Val), D-phenylalanine (D-Phe), D-leucine (D-Leu), D-tyrosine (D-Tyr), D-cysteine (D-Cys), D-tryptophan (D-Trp), D-citrulline (D-CIT), D-carnosine (D-CARN), and the like. In connection with the embodiments described herein, amino acids can be covalently attached to other portions of the compounds described herein through their alpha-amino and carboxy functional groups (i.e. in a peptide bond configuration), or through their side chain functional groups (such as the side chain carboxy group in glutamic acid) and either their alpha-amino or carboxy functional groups. It will be understood that amino acids, when used in connection with the compounds described herein, may exist as zwitterions in a compound in which they are incorporated.

DETAILED DESCRIPTION OF THE INVENTION

As used herein "etarfolatide" is the compound of formula:

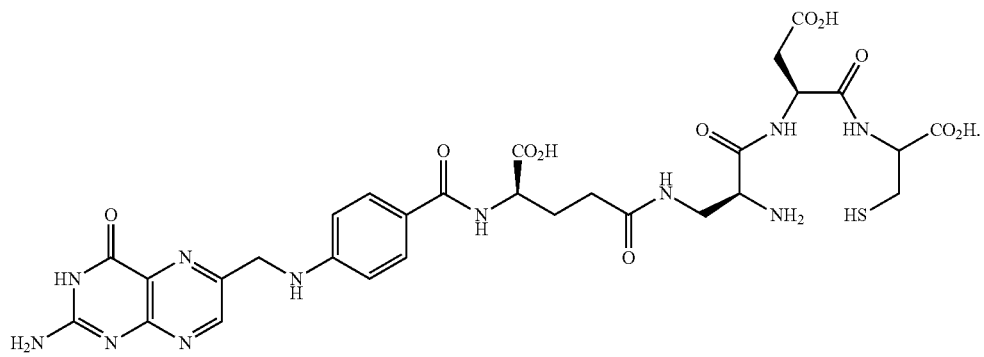 [SMILES: Nc1nc2ncc(CNc3ccc(C(=O)N[C@H](CCC(=O)NC[C@H](N)C(=O)N[C@@H](CC(=O)O)C(=O)NC(CS)C(=O)O)C(=O)O)cc3)nc2c(=O)[nH]1]

Several embodiments are described by the following enumerated clauses:

1. A method of imaging a cancer, the method comprising administering to a patient an unlabeled compound according to Formula I

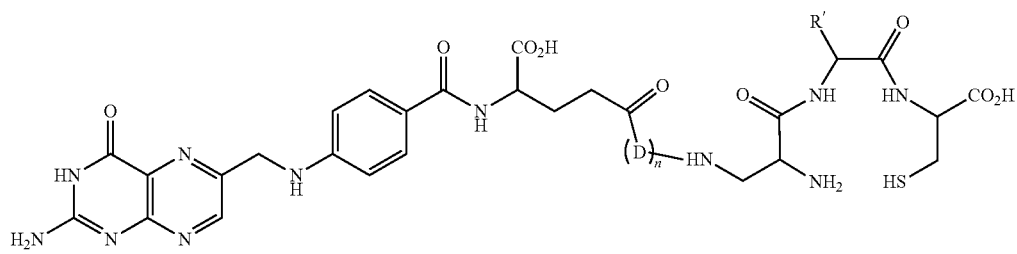

or a pharmaceutically acceptable salt thereof, wherein R' is hydrogen, or R' is selected from the group consisting of alkyl, aminoalkyl, carboxyalkyl, hydroxyalkyl, heteroalkyl, aryl, arylalkyl and heteroarylalkyl, each of which is optionally substituted, wherein D is a divalent linker, and wherein n is 0 or 1, and administering to the patient a labeled compound according to Formula II

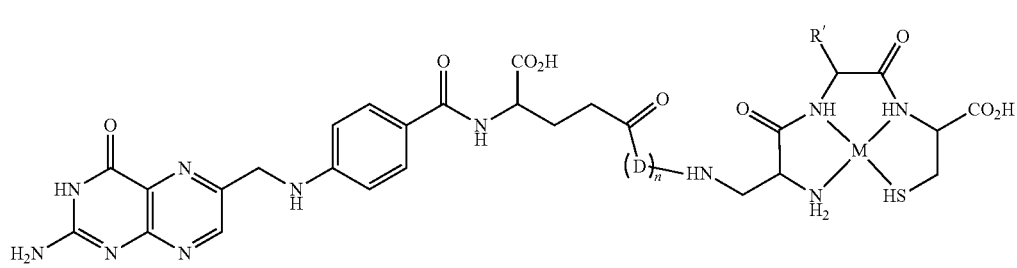

or a pharmaceutically acceptable salt thereof, wherein R' is hydrogen, or R' is selected from the group consisting of alkyl, aminoalkyl, carboxyalkyl, hydroxyalkyl, heteroalkyl, aryl, arylalkyl and heteroarylalkyl, each of which is optionally substituted, wherein D is a divalent linker, wherein n is 0 or 1, and wherein M is a cation of a radionuclide.

2. The method of clause 1, wherein the unlabeled compound is of the formula

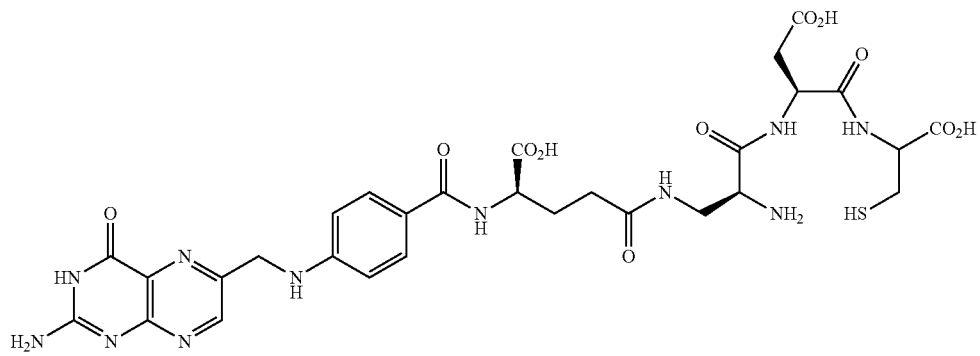 [SMILES: Nc1nc2ncc(CNc3ccc(C(=O)N[C@H](CCC(=O)NC[C@H](N)C(=O)N[C@@H](CC(=O)O)C(=O)NC(CS)C(=O)O)C(=O)O)cc3)nc2c(=O)[nH]1]

or a pharmaceutically acceptable salt thereof, and the labeled compound is of the formula

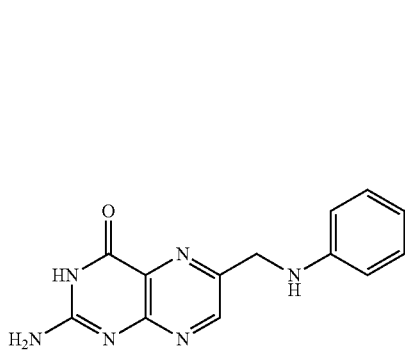 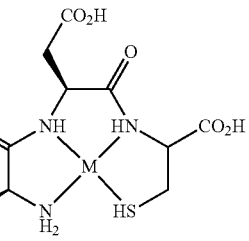

or a pharmaceutically acceptable salt thereof, and wherein M is a cation of a radionuclide.

3. The method of any of the preceding clauses wherein the patient is administered the unlabeled compound, or a pharmaceutically acceptable salt thereof, before the patient is administered the labeled compound, or a pharmaceutically acceptable salt thereof.

4. The method of any of the preceding clauses, wherein the cancer is selected from the group consisting of lung cancer, bone cancer, pancreatic cancer, skin cancer, cancer of the head, cancer of the neck, cutaneous melanoma, intraocular melanoma uterine cancer, ovarian cancer, endometrial cancer, rectal cancer, stomach cancer, colon cancer, breast cancer, triple negative breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, nonsmall cell lung cancer, cancer of the adrenal gland, sarcoma of soft tissue, cancer of the urethra, prostate cancer, chronic leukemia, acute leukemia, lymphocytic lymphoma, pleural mesothelioma, cancer of the bladder, Burkitt's lymphoma, cancer of the ureter, cancer of the kidney, renal cell carcinoma, carcinoma of the renal pelvis, neoplasms of the central nervous system (CNS), primary CNS lymphoma, spinal axis tumors, brain stem glioma, pituitary adenoma, and adenocarcinoma of the gastroesophageal junction.

5. The method of any of the preceding clauses wherein the cancer being imaged is a tumor.

6. The method of any of the preceding clauses wherein the cancer is malignant.

7. The method of any of the preceding clauses wherein the cancer is a folate receptor expressing cancer.

8. The method of any of the preceding clauses wherein the cancer is an endometrial cancer.

9. The method of any of clauses 1-7 wherein the cancer is a non-small cell lung cancer.

10. The method of any of clauses 1-7 wherein the cancer is an ovarian cancer.

11. The method of any of clauses 1-7 wherein the cancer is a triple negative breast cancer.

12. The method of any of the preceding clauses wherein the radionuclide is selected from the group consisting of an isotope of gallium, an isotope of indium, an isotope of copper, an isotope of technetium, and an isotope of rhenium.

13. The method of any of clauses 1-12 wherein the radionuclide is an isotope of gallium.

14. The method of any of clauses 1-12 wherein the radionuclide is an isotope of indium.

15. The method of any of clauses 1-12 wherein the radionuclide is an isotope of copper.

16. The method of any of clauses 1-12 wherein the radionuclide is an isotope of technetium.

17. The method of any of clauses 1-12 wherein the radionuclide is an isotope of rhenium.

18. The method of any of the preceding clauses wherein the cancer is imaged about 0.5 hours to about 8 hours after administration of the labeled compound, or a pharmaceutically acceptable salt thereof.

19. The method of any of clauses 1-17 wherein the cancer is imaged about 0.5 hours to about 6 hours after administration of the labeled compound, or a pharmaceutically acceptable salt thereof.

20. The method of any of clauses 1-17 wherein the cancer is imaged about 0.5 hours to about 4 hours after administration of the labeled compound, or a pharmaceutically acceptable salt thereof.

21. The method of any of clauses 1-17 wherein the cancer is imaged about 1 hour to about 3 hours after administration of the labeled compound, or a pharmaceutically acceptable salt thereof.

22. The method of any of clauses 1-21 wherein the patient is administered about a 2-fold to about a 1000-fold excess of the unlabeled compound, or a pharmaceutically acceptable salt thereof, relative to the labeled compound, or pharmaceutically acceptable salt thereof.

23. The method of any of clauses 1-21 wherein the patient is administered about a 2-fold to about a 100-fold excess of the unlabeled compound, or a pharmaceutically acceptable salt thereof, relative to the labeled compound, or pharmaceutically acceptable salt thereof.

24. The method of any of clauses 1-21 wherein the patient is administered about a 2-fold to about a 30-fold excess of the unlabeled compound, or a pharmaceutically acceptable salt thereof, relative to the labeled compound, or pharmaceutically acceptable salt thereof.

25. The method of any of clauses 1-21 wherein the patient is administered about a 2-fold to about a 10-fold excess of the unlabeled compound, or a pharmaceutically acceptable salt thereof, relative to the labeled compound, or pharmaceutically acceptable salt thereof.

26. The method of any of clauses 1-21 wherein the patient is administered about 0.1 mg to about 20 mg of the unlabeled compound, or a pharmaceutically acceptable salt thereof, and the patient is administered about 0.01 mg to about 2 mg of the labeled compound, or a pharmaceutically acceptable salt thereof.

27. The method of any of clauses 1-21 wherein the patient is administered about 0.3 mg to about 10 mg of the unlabeled compound, or a pharmaceutically acceptable salt thereof, and the patient is administered about 0.05 mg to about 0.5 mg of the labeled compound, or a pharmaceutically acceptable salt thereof.

28. The method of any of clauses 1-21 wherein the patient is administered a mass dose of about 50 nmol/kg to about 3000 nmol/kg of patient body weight of the unlabeled compound, or a pharmaceutically acceptable salt thereof, and the labeled compound, or a pharmaceutically acceptable salt thereof.

29. The method of any of clauses 1-21 wherein the patient is administered a mass dose of about 50 nmol/kg to about 500 nmol/kg of patient body weight of the unlabeled compound, or a pharmaceutically acceptable salt thereof, and the labeled compound, or a pharmaceutically acceptable salt thereof.

30. The method of any of clauses 1-21 wherein the patient is administered a mass dose of about 50 nmol/kg to about 400 nmol/kg of patient body weight of the unlabeled compound, or a pharmaceutically acceptable salt thereof, and the labeled compound, or a pharmaceutically acceptable salt thereof.

31. The method of any of clauses 1-21 wherein the patient is administered a mass dose of about 100 nmol/kg to about 300 nmol/kg of patient body weight of the unlabeled compound, or a pharmaceutically acceptable salt thereof, and the labeled compound, or a pharmaceutically acceptable salt thereof.

32. The method of any of clauses 1-21 wherein the patient is administered a mass dose of about 100 nmol/kg of patient body weight of the unlabeled compound, or a pharmaceutically acceptable salt thereof, and the labeled compound, or a pharmaceutically acceptable salt thereof.

33. The method of any of the preceding clauses wherein the patient is administered the unlabeled compound or a pharmaceutically acceptable salt thereof, over a period of about 15 seconds to about 2 minutes.

34. The method of any of the preceding clauses wherein the patient is administered the unlabeled compound, or a pharmaceutically acceptable salt thereof, over a period of about 30 seconds to about 90 seconds.

35. The method of any of the preceding clauses wherein the patient is administered the labeled compound, or a pharmaceutically acceptable salt thereof, over a period of about 15 seconds to about 2 minutes.

36. The method of any of the preceding clauses wherein the patient is administered the unlabeled compound, or a pharmaceutically acceptable salt thereof, about 30 seconds to about 5 minutes before the patient is administered the labeled compound, or a pharmaceutically acceptable salt thereof.

37. The method of any of the preceding clauses wherein the patient is administered the unlabeled compound, or a pharmaceutically acceptable salt thereof, about 1 minute to about 2 minutes before the patient is administered the labeled compound, or a pharmaceutically acceptable salt thereof.

38. The method of any of the preceding clauses wherein the patient is administered saline after the patient is administered the labeled compound, or a pharmaceutically acceptable salt thereof.

39. The method of any of the preceding clauses wherein the cancer is imaged by PET imaging.

40. The method of any of clauses 1-38 wherein the cancer is imaged by MRI imaging.

41. The method of any of clauses 1-38 wherein the cancer is imaged by SPECT/CT imaging.

42. The method of any of the preceding clauses further comprising the step of measuring an amount of radioactivity of the cancer and an amount of radioactivity of a control tissue.

43. The method clause 42 wherein the control tissue is selected from the group consisting of blood, liver, lung, spleen, intestine, heart, kidney, and muscle.

44. The method of clause 42 or clause 43 wherein the amount of radioactivity of the cancer is compared to the amount of radioactivity of aortic arch blood.

45. The method of clause 42 or clause 43 wherein the amount of radioactivity of the cancer is compared to the amount of radioactivity of muscle.

46. The method of clause 42 or clause 43 wherein the amount of radioactivity of the cancer is compared to the amount of radioactivity of lung.

47. The method of clause 42 or clause 43 wherein the amount of radioactivity of the cancer is compared to the amount of radioactivity of the kidney.

48. The method of any of clauses 42-47 further comprising the step of calculating a tumor to background ratio as a quotient of the amount of radioactivity of the cancer compared to the amount of radioactivity of the control tissue.

49. The method of clause 48 wherein the tumor to background ratio is greater than about 2.

50. The method of clause 48 wherein the tumor to background ratio is about 2 to about 150.

51. The method of any of the preceding clauses wherein the labeled compound comprises about 20 mCi to about 25 mCi of technetium-99m.

52. The method of any of the preceding clauses wherein the patient has not taken a folic acid supplement within about 3 weeks of the administration of the labeled compound.

53. The method of any of the preceding clauses wherein the imaged cancer is visually assessed.

54. The method of any of the preceding clauses wherein multiple doses of the unlabeled compound, or a pharmaceutically acceptable salt thereof, and the labeled compound, or a pharmaceutically acceptable salt thereof, are administered.

55. The method of any of the preceding clauses wherein the labeled compound, or a pharmaceutically acceptable salt thereof, is administered to the patient, the unlabeled compound, or a pharmaceutically acceptable salt thereof, is then administered to the patient, and the labeled compound, or a pharmaceutically acceptable salt thereof, is administered to the patient a second time after the unlabeled compound, or a pharmaceutically acceptable salt thereof, is administered to the patient.

56. The method of clause 55 wherein the labeled compound, or a pharmaceutically acceptable salt thereof, is first administered to the patient on day 1 and the unlabeled compound, or a pharmaceutically acceptable salt thereof, and the labeled compound, or a pharmaceutically acceptable salt thereof, are then administered to the patient on day 4 to day 10.

57. The method of clause 55 wherein the labeled compound, or a pharmaceutically acceptable salt thereof, is first administered to the patient on day 1 and the unlabeled compound, or a pharmaceutically acceptable salt thereof, and the labeled compound, or a pharmaceutically acceptable salt thereof, are then administered to the patient on day 5 to day 8.

58. The method of any of clauses 55 to 57 wherein the patient is administered about 0.3 mg to about 10 mg of the unlabeled compound, or a pharmaceutically acceptable salt thereof, and the patient is administered about 0.05 mg to about 0.5 mg of the labeled compound, or a pharmaceutically acceptable salt thereof, each time the labeled compound, or a pharmaceutically acceptable salt thereof, is administered to the patient.

59. The method of any of clauses 55 to 58 wherein the patient is imaged after each administration of the labeled compound, or a pharmaceutically acceptable salt thereof.

60. The method of clause 48, wherein the tumor to background ratio is at least 4.

61. The method of clause 48, wherein the tumor to background ratio is at least 5.

66. The method of clause 48, wherein the tumor to background ratio is at least 10.

67. The method of clause 48, wherein the tumor to background ratio is at least 15.

68. The method of clause 48, wherein the tumor to background ratio is at least 20.

69. The method of clause 48, wherein the tumor to background ratio is at least 25.

70. The method of clause 48, wherein the tumor to background ratio is at between about 2 and about 10.

71. The method of clause 48, wherein the tumor to background ratio is at between about 2 and about 5.

72. The method of clause 48, wherein the tumor to background ratio is at between about 2 and about 4.

As described herein, a "patient" can be administered the unlabeled compound or the labeled compound described herein, and the patient can be a human or, in the case of veterinary applications, the patient can be a laboratory, an agricultural, a domestic, or a wild animal. In one aspect, the patient can be a laboratory animal such as a rodent (e.g., mouse, rat, hamster, etc.), a rabbit, a monkey, a chimpanzee, a domestic animal such as a dog, a cat, or a rabbit, an agricultural animal such as a cow, a horse, a pig, a sheep, a goat, or a wild animal in captivity such as a bear, a panda, a lion, a tiger, a leopard, an elephant, a zebra, a giraffe, a gorilla, a dolphin, or a whale.

In one embodiment, the unlabeled compound can be of Formula I

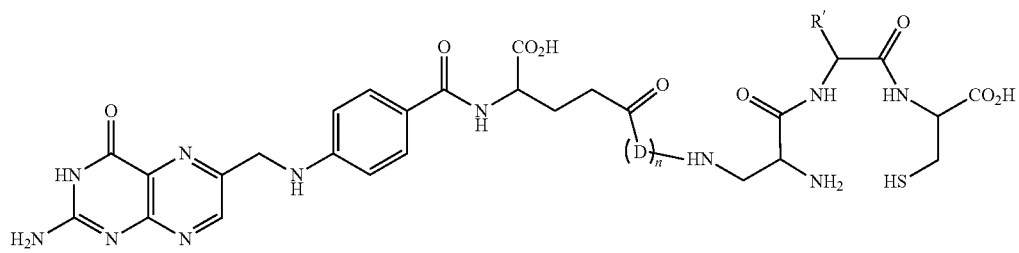

I or a pharmaceutically acceptable salt thereof, wherein R' is hydrogen, or R' is selected from the group consisting of alkyl, aminoalkyl, carboxyalkyl, hydroxyalkyl, heteroalkyl, aryl, arylalkyl and heteroarylalkyl, each of which is optionally substituted, wherein D is a divalent linker, and wherein n is 0 or 1. In another embodiment, the unlabeled compound can be of the formula

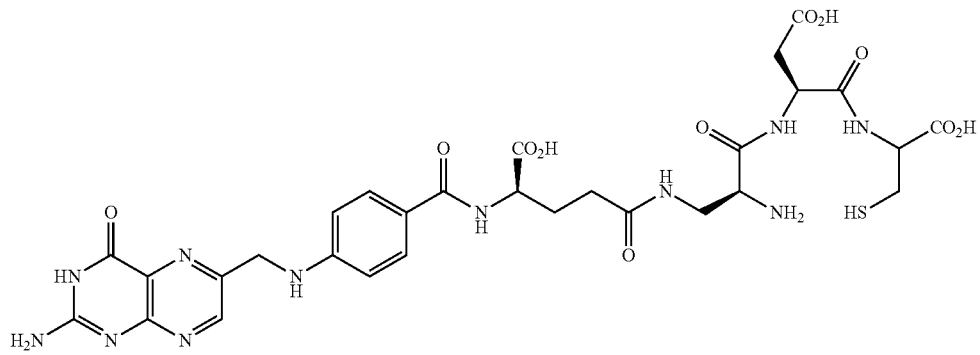 [SMILES: Nc1nc2ncc(CNc3ccc(C(=O)N[C@H](CCC(=O)NC[C@H](N)C(=O)N[C@@H](CC(=O)O)C(=O)NC(CS)C(=O)O)C(=O)O)cc3)nc2c(=O)[nH]1]

or a pharmaceutically acceptable salt thereof.

In one embodiment, the labeled compound can be of the Formula II

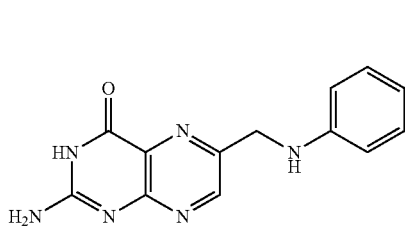 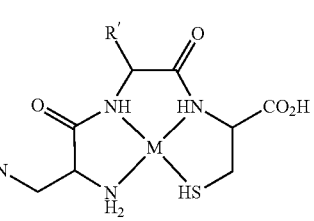

II or a pharmaceutically acceptable salt thereof, wherein R' is hydrogen, or R' is selected from the group consisting of alkyl, aminoalkyl, carboxyalkyl, hydroxyalkyl, heteroalkyl, aryl, arylalkyl and heteroarylalkyl, each of which is optionally substituted, wherein D is a divalent linker, wherein n is 0 or 1, and wherein M is a cation of a radionuclide. In yet another embodiment, the labeled compound can be of the formula

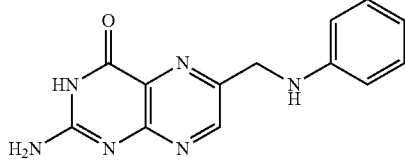 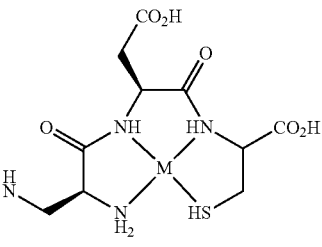

or a pharmaceutically acceptable salt thereof, and wherein M is a cation of a radionuclide.

In one embodiment, the radionuclide is selected from the group consisting of an isotope of gallium, an isotope of indium, an isotope of copper, an isotope of technetium, and an isotope of rhenium. In other embodiments, the radionuclide is an isotope of technetium (e.g., 99m-technetium).

As used herein, the term "pharmaceutically acceptable salt" refers to those salts whose counter ions may be used in pharmaceuticals. Such salts include:

(1) acid addition salts, which can be obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methane sulfonic acid, ethanesulfonic acid, p-toluenesulfonic acid, salicylic acid, tartaric acid, citric acid, succinic acid or malonic acid and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, trimethamine, N-methylglucamine, and the like.

Pharmaceutically acceptable salts are well-known to those skilled in the art, and any such pharmaceutically acceptable salt may be contemplated in connection with the embodiments described herein.

In various embodiments, suitable acid addition salts are formed from acids which form non-toxic salts. Illustrative examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

In various embodiments, suitable base salts of the unlabeled and the labeled compounds described herein are formed from bases which form non-toxic salts. Illustrative examples include the arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts.

As used herein, "optionally" means that the subsequently described event or circumstance may but need not occur, and that the description includes instances where the event or circumstance occurs and instances in which it does not. For example, "aryl group optionally substituted with an alkyl group" means that the alkyl may, but need not, be present, and the description includes situations where the aryl group is substituted with an alkyl group and situations where the aryl group is not substituted with the alkyl group.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

In one illustrative aspect, the unlabeled compounds or the labeled compounds described herein may contain one or more chiral centers, or may otherwise be capable of existing as multiple stereoisomers. Accordingly, various embodiments may include pure stereoisomers as well as mixtures of stereoisomers, such as enantiomers, diastereomers, and enantiomerically or diastereomerically enriched mixtures. In one aspect, the unlabeled compounds and labeled compounds described herein may be capable of existing as geometric isomers. Accordingly, various embodiments may include pure geometric isomers or mixtures of geometric isomers.

In some aspects, the unlabeled or labeled compounds described herein may exist in unsolvated forms as well as solvated forms, including hydrated forms. In general, the solvated forms are equivalent to unsolvated forms and are encompassed within the scope of the present invention.

In one illustrative aspect, the chemical linkage (e.g. "D" or "divalent linker") in the unlabeled or labeled compound described herein can be a direct linkage or the linkage can be through an intermediary linker. In one embodiment, if present, an intermediary linker can be any biocompatible linker known in the art. In one illustrative embodiment, the divalent linker comprises about 1 to about 30 carbon atoms. In another illustrative embodiment, the divalent linker comprises about 2 to about 20 carbon atoms. In other embodiments, lower molecular weight divalent linkers (i.e., those having an approximate molecular weight of about 30 to about 300) are employed.

In one embodiment, the divalent linker comprises a heteroatom directly bonded to the folate or to the chelator. In one embodiment, the heteroatom is nitrogen. In another embodiment, the divalent linker comprises an optionally-substituted diaminoalkylene. In one embodiment, the optionally-substituted diaminoalkylene is a diaminoacid. In another embodiment, the divalent linker comprises one or more optionally-substituted diaminoalkylene moieties, and one or more optionally-substituted amino acids.

In another illustrative embodiment, the divalent linker includes one or more amino acids. In one variation, the divalent linker includes a single amino acid. In another variation, the divalent linker includes a peptide having from 2 to about 50, 2 to about 30, or 2 to about 20 amino acids. In another variation, the divalent linker includes a peptide having from about 4 to about 8 amino acids. Such amino acids are illustratively selected from the naturally occurring amino acids, or stereoisomers thereof. In another embodiment, the amino acid may also be any other amino acid, such as any amino acid having the general formula:

—N(R$^1$)—(CR$^2$R$^3$)$_q$—C(O)— where R$^1$ is hydrogen, alkyl, acyl, or a suitable nitrogen protecting group, R$^2$ and R$^3$ in the amino acid are hydrogen or a substituent, each of which is independently selected in each occurrence, and q is an integer such as 1, 2, 3, 4, or 5.

Illustratively, R$^2$ and/or R$^3$ in the amino acid independently correspond to, but are not limited to, hydrogen or the side chains present on naturally occurring amino acids, such as methyl, benzyl, hydroxymethyl, thiomethyl, carboxyl, carboxylmethyl, guanidinopropyl, and the like, and derivatives and protected derivatives thereof. The above described formula includes all stereoisomeric variations. For example, the amino acid may be selected from asparagine, aspartic acid, cysteine, glutamic acid, lysine, glutamine, arginine, serine, ornithine, threonine, and the like. In one variation, the divalent linker includes at least 2 amino acids selected from asparagine, aspartic acid, cysteine, glutamic acid, lysine, glutamine, arginine, serine, ornithine, and threonine. In another variation, the divalent linker includes between 2 and about 5 amino acids selected from asparagine, aspartic acid, cysteine, glutamic acid, lysine, glutamine, arginine, serine, ornithine, and threonine. In another variation, the divalent linker includes a tripeptide, tetrapeptide, pentapeptide, or hexapeptide consisting of amino acids selected from aspartic acid, cysteine, glutamic acid, lysine, arginine, and ornithine, and combinations thereof.

In another embodiment, the divalent linker may also include one or more spacer linkers. Illustrative spacer linkers are shown in the following table. The following non-limiting, illustrative spacer linkers are described where * indicates the point of attachment to the folate or the chelator in the unlabeled compound or the labeled compound.

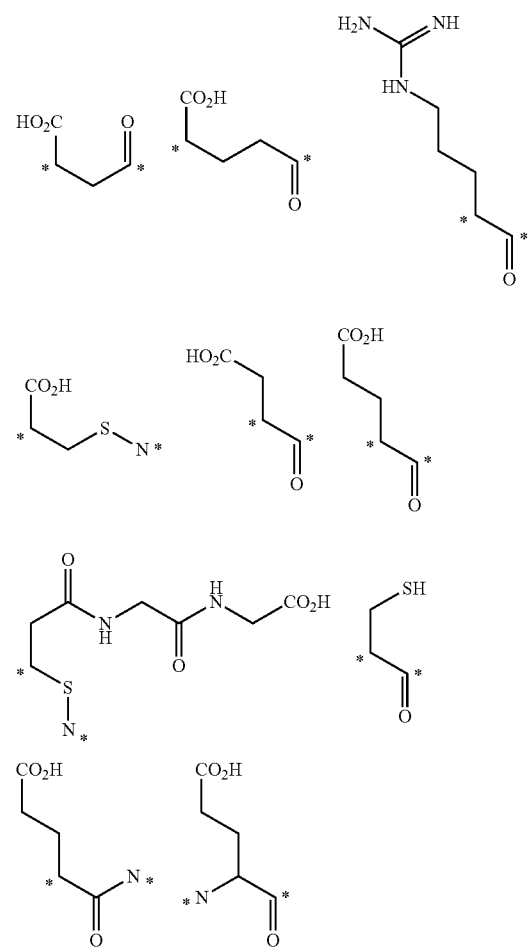

-continued

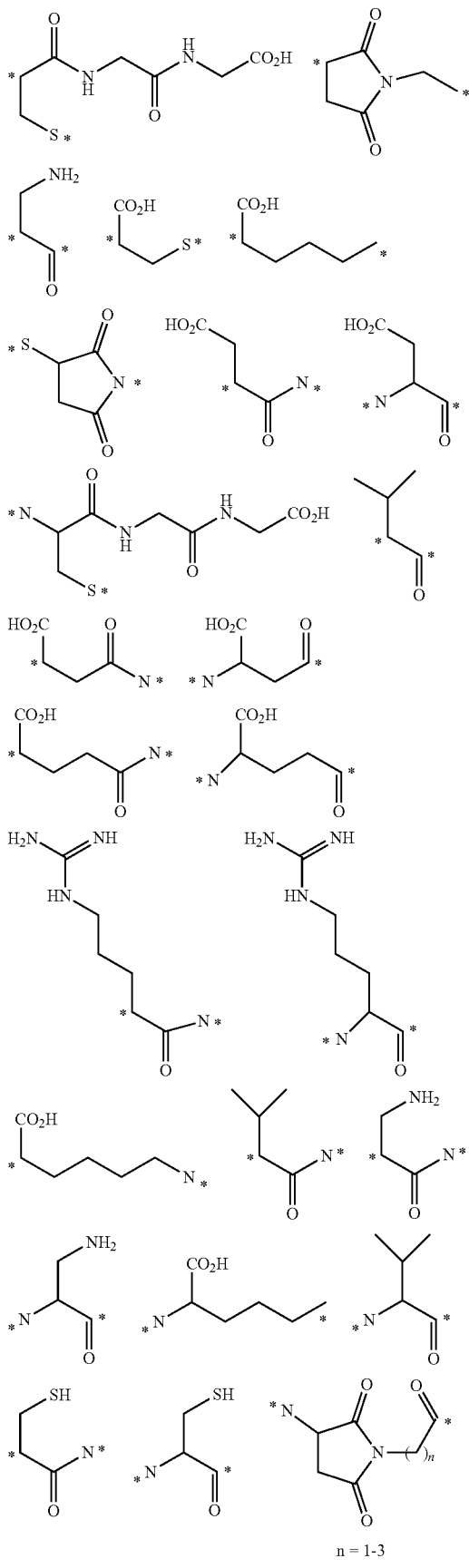

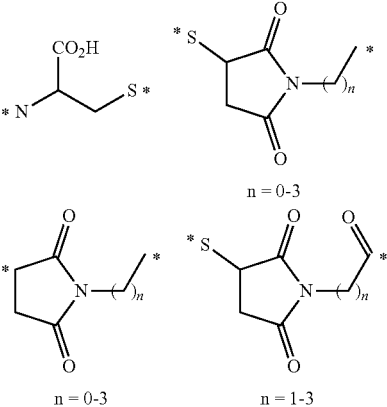

In illustrative embodiments, the labeled compound can be labeled with $^{99m}$Tc. Typical methods known in the art for labelling with $^{99m}$Tc include, but are not limited to, the reduction of pertechnetate ions in the presence of a chelating precursor to form the labile $^{99m}$Tc-precursor complex, which, in turn, reacts with a metal binding group. The reducing agent can be, for example, $SnCl_2$. Stannous ion is readily available as its dehydrate (such as tin chloride dihydrate, $SnCl_2.2H_2O$), or it can be generated in situ from tin metal (such as foil, granules, powder, turnings and the like) by contacting with aqueous acid (such as HCl). The stannous ion solution can be prepared by dissolving $SnCl_2.2H_2O$ in aqueous HCl at a concentration preferred for a particular application.

In various embodiments, the labeled compound may be prepared at a designated nuclear pharmacy by reconstitution with Sodium Pertechnetate Tc-99m Injection, U.S.P., as per the Nuclear Pharmacy Manual, which is expressly incorporated by reference herein. In another embodiment, the labeled compound may be prepared by a method described in U.S. Appl. Publication No. 2004/0033195, which is expressly incorporated by reference herein.

In various embodiments, the labeled compound comprises from about 5 mCi to about 100 mCi, about 5 mCi to about 80 mCi, about 5 mCi to about 50 mCi, about 10 mCi to about 30 mCi, or about 20 mCi to about 25 mCi of the radioisotope.

In various embodiments, the cancer is a carcinoma, a sarcoma, a lymphoma, a melanoma, a mesothelioma, a nasopharyngeal carcinoma, a leukemia, an adenocarcinoma, or a myeloma. In other embodiments, the cancer may be lung cancer, bone cancer, pancreatic cancer, skin cancer, cancer of the head, cancer of the neck, cutaneous melanoma, intraocular melanoma uterine cancer, ovarian cancer, endometrial cancer, rectal cancer, stomach cancer, colon cancer, breast cancer, triple negative breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, non-small cell lung cancer, cancer of the adrenal gland, sarcoma of soft tissue, cancer of the urethra, prostate cancer, chronic leukemia, acute leukemia, a lymphocytic lymphoma, pleural mesothelioma, cancer of the bladder, Burkitt's lymphoma, cancer of the ureter, cancer of the kidney, renal cell carcinoma, carcinoma of the renal pelvis, a neoplasm of the central nervous system (CNS), primary CNS lymphoma, a spinal axis tumor, a brain stem glioma, a pituitary adenoma, or an adenocarcinoma of the gastroesophageal junction.

In some aspects of these embodiments, the cancer is a folate receptor expressing cancer. In some aspects of these embodiments, the cancer is an endometrial cancer, a non-small cell lung cancer, an ovarian cancer, or a triple-negative breast cancer. In another embodiment, the cancer being imaged is a tumor. In another embodiment, the cancer is malignant.

In some aspects of these embodiments, the methods described herein may be used to image a site of inflammation in a patient.

As described herein, the term "administering" includes all means of introducing the unlabeled or labeled compounds described herein to the patient, including, but not limited to, oral (po), intravenous (iv), intramuscular (im), subcutaneous (sc), transdermal, and the like. The unlabeled and labeled compounds described herein may be administered in unit dosage forms and/or formulations containing conventional nontoxic pharmaceutically-acceptable carriers, adjuvants, and vehicles.

In one aspect, an unlabeled or labeled compound as described herein may be administered directly into the blood stream, into muscle, or into an internal organ. Suitable routes for such parenteral administration include intravenous, intraarterial, intraperitoneal, intrathecal, epidural, intracerebroventricular, intraurethral, intrasternal, intracranial, intratumoral, intramuscular and subcutaneous delivery. In one embodiment, means for parenteral administration include needle (including microneedle) injectors, needle-free injectors and infusion techniques.

In one illustrative aspect, parenteral formulations are typically aqueous solutions which may contain carriers or excipients such as salts, carbohydrates and buffering agents (preferably at a pH of from 3 to 9), but they may be more suitably formulated as a sterile non-aqueous solution or as a dried form to be used in conjunction with a suitable vehicle such as sterile, pyrogen-free water or sterile saline. In other embodiments, any of the liquid formulations described herein may be adapted for parenteral administration of the unlabeled or labeled compounds as described herein. The preparation under sterile conditions, by lyophilization to produce a sterile lyophilized powder for a parenteral formulation, may readily be accomplished using standard pharmaceutical techniques well-known to those skilled in the art. In one embodiment, the solubility of an unlabeled or labeled compound used in the preparation of a parenteral formulation may be increased by the use of appropriate formulation techniques, such as the incorporation of solubility-enhancing agents.

In illustrative embodiments, the patient may be administered the unlabeled or labeled compound over a period of time. In various embodiments, the length of time may be from about 15 seconds to about 10 minutes, about 15 seconds to about 9 minutes, about 15 seconds to about 8 minutes, about 15 seconds to about 7 minutes, about 15 seconds to about 6 minutes, about 15 seconds to about 5 minutes, about 15 seconds to about 4 minutes, about 15 seconds to about 3 minutes, about 15 seconds to about 2 minutes, about 15 seconds to about 1 minute, about 15 seconds to about 30 seconds, or about 30 seconds to 90 seconds. In other embodiments, the length of time can be any time between about 15 seconds and about 10 minutes, including but not limited to, about 15, 30, 45, or 90 seconds, or about 1, 2, 3, 4, 5, 6, 7, 8, 9, or 10 minutes. In one aspect, the unlabeled or labeled compound may be administered in a single dose or multiple doses.

In various illustrative embodiments the patient is administered an excess of the unlabeled compound compared to the labeled compound. For example, the excess can be from about 2-fold to about 1000-fold, about 2-fold to about 500-fold, about 2-fold to about 400-fold, about 2-fold to about 300-fold, about 2-fold to about 200-fold, about 2-fold to about 100-fold, about 2-fold to about 90-fold, about 2-fold to about 80-fold, about 2-fold to about 70-fold, about 2-fold to about 60-fold, about 2-fold to about 50-fold, about 2-fold to about 40-fold, about 2-fold to about 30-fold, about 2-fold to about 20-fold, about 2-fold to about 10-fold, about 2-fold to about 5-fold, about 2-fold to about 4-fold, or about 2-fold to about 3-fold.

The amount of the unlabeled compound or the labeled compound, or the total of the unlabeled compound and the labeled compound together, to be administered can vary significantly depending on the cancer being imaged, the route of administration of the unlabeled or labeled compound, and the tissue distribution. The amount to be administered to a patient can be based on body surface area, mass, and physician assessment. In various embodiments, amounts to be administered can range, for example, from about 0.05 mg to about 30 mg, 0.05 mg to about 25.0 mg, about 0.05 mg to about 20.0 mg, about 0.05 mg to about 15.0 mg, about 0.05 mg to about 10.0 mg, about 0.05 mg to about 9.0 mg, about 0.05 mg to about 8.0 mg, about 0.05 mg to about 7.0 mg, about 0.05 mg to about 6.0 mg, about 0.05 mg to about 5.0 mg, about 0.05 mg to about 4.0 mg, about 0.05 mg to about 3.0 mg, about 0.05 mg to about 2.0 mg, about 0.05 mg to about 1.0 mg, about 0.05 mg to about 0.5 mg, about 0.05 mg to about 0.4 mg, about 0.05 mg to about 0.3 mg, about 0.05 mg to about 0.2 mg, about 0.05 mg to about 0.1 mg, about 0.01 mg to about 2 mg, about 0.3 mg to about 10 mg, about 0.1 mg to about 20 mg, or about 0.8 to about 3 mg. One of skill in the art will readily appreciate that the dose may vary within the various ranges provided above based on the factors noted above, and may be at the physician's discretion.

As described herein, the term "mass dose" means the amount of unlabeled compound and labeled compound administered to the patient. The mass dose can vary significantly depending on the cancer being imaged, the route of administration of the unlabeled compound and the labeled compound, and tissue distribution. In various embodiments, the mass dose can range, for example, from about 50 nmol/kg to about 3000 nmol/kg of patient body weight, about 50 nmol/kg to about 2000 nmol/kg, about 50 nmol/kg to about 1000 nmol/kg, about 50 nmol/kg to about 900 nmol/kg, about 50 nmol/kg to about 800 nmol/kg, about 50 nmol/kg to about 700 nmol/kg, about 50 nmol/kg to about 600 nmol/kg, about 50 nmol/kg to about 500 nmol/kg, about 50 nmol/kg to about 400 nmol/kg, about 50 nmol/kg to about 300 nmol/kg, about 50 nmol/kg to about 200 nmol/kg, about 50 nmol/kg to about 100 nmol/kg, about 100 nmol/kg to about 300 nmol/kg, about 100 nmol/kg to about 500 nmol/kg, about 100 nmol/kg to about 1000 nmol/kg, about 100 nmol/kg to about 2000 nmol/kg of patient body weight, or any ranges of amounts in the preceding paragraph. In other embodiments, the mass dose may be about 100 nmol/kg, about 150 nmol/kg, about 200 nmol/kg, about 250 nmol/kg, about 300 nmol/kg, about 350 nmol/kg, about 400 nmol/kg, about 450 nmol/kg, about 500 nmol/kg, about 600 nmol/kg, about 700 nmol/kg, about 800 nmol/kg, about 900 nmol/kg, about 1000 nmol/kg, about 2000 nmol/kg, or about 3000 nmol/kg of patient body weight. In these embodiments, "kg" is kilograms of patient body weight. In one aspect, the mass dose of the unlabeled compound and labeled compound may be administered in multiple doses of the unlabeled and the labeled compound.

In an illustrative embodiment, the patient is administered the unlabeled compound before the patient is administered the labeled compound. The length of time between administering the patient the unlabeled compound and administering the patient the labeled compound can vary. For example, the length of time between administering the patient the unlabeled compound and administering the patient the labeled compound can range from about 15 seconds to about 10 minutes, about 15 seconds to about 9 minutes, about 15 seconds to about 8 minutes, about 15 seconds to about 7 minutes, about 15 seconds to about 6 minutes, about 15 seconds to about 5 minutes, about 15 seconds to about 4 minutes, about 15 seconds to about 3 minutes, about 15 seconds to about 2 minutes, about 15 seconds to about 1 minute, about 15 seconds to about 30 seconds, or about 1 to about 2 minutes.

In an illustrative embodiment, the patient is administered the labeled compound, and imaged after a period of time. In various aspects, the length of time between administering the labeled compound and imaging the patient can range, for example, from about 30 minutes to about 8 hours, about 30 minutes to about 7 hours, about 30 minutes to about 6 hours, about 30 minutes to about 5 hours, about 30 minutes to about 4 hours, about 30 minutes to about 3 hours, about 30 minutes to about 2 hours, about 30 minutes to about 1 hour, about 1 hour to about 8 hours, about 1 hour to about 7 hours, about 1 hour to about 6 hours, about 1 hour to about 5 hours, about 1 hour to about 4 hours, about 1 hour to about 3 hours, about 4 hours to about 6 hours, or about 1 hour to about 2 hours. The length of time may vary at the physician's discretion. In other illustrative embodiments, the patient is imaged multiple times during any of these time periods.

In one illustrative aspect, the labeled compound, or a pharmaceutically acceptable salt thereof, is administered to the patient, the unlabeled compound, or a pharmaceutically acceptable salt thereof, is then administered to the patient, and the labeled compound, or a pharmaceutically acceptable salt thereof, is administered to the patient a second time after the unlabeled compound, or a pharmaceutically acceptable salt thereof, is administered to the patient. In this aspect, the labeled compound, or a pharmaceutically acceptable salt thereof, may first be administered to the patient on day 1 and the unlabeled compound, or a pharmaceutically acceptable salt thereof, and the labeled compound, or a pharmaceutically acceptable salt thereof, may then be administered to the patient on day 4 to day 10. In another aspect, the labeled compound, or a pharmaceutically acceptable salt thereof, may first be administered to the patient on day 1 and the unlabeled compound, or a pharmaceutically acceptable salt thereof, and the labeled compound, or a pharmaceutically acceptable salt thereof, may then be administered to the patient on day 5 to day 8. In these illustrative aspects, the patient may be administered about 0.3 mg to about 10 mg of the unlabeled compound, or a pharmaceutically acceptable salt thereof, and the patient may be administered about 0.05 mg to about 0.5 mg of the labeled compound, or a pharmaceutically acceptable salt thereof, each time the labeled compound, or a pharmaceutically acceptable salt thereof, is administered to the patient. In these illustrative embodiments, the patient may be imaged after each administration of the labeled compound, or a pharmaceutically acceptable salt thereof.

In one embodiment of the method described herein, the cancer is imaged. In yet another illustrative embodiment, a control tissue is also imaged. In one illustrative embodiment, imaging occurs by PET imaging. In other illustrative embodiments imaging occurs by MRI imaging or SPECT/CT imaging. It is appreciated by one skilled in the art that the imaging method can be any suitable imaging method known in the art.

In an illustrative embodiment, the images produced by the methods described herein can be quantified. In one aspect, regions of interest can be identified and quantified within the images, as described herein, for example, in the "Examples" section of this patent application. In an illustrative embodiment the pixel density of an image is measured in a region of interest. In illustrative embodiments, pixel density is related to the amount of radioactivity in the area being imaged. In various aspects, the images described herein can be quantified by many different types of methods. In one embodiment, the imaged cancer is visually assessed.

In illustrative embodiments, the method comprises measuring the radioactivity of the cancer and a control tissue. In one embodiment, a "control tissue" can be a body fluid or a tissue and the amount of radioactivity of the control tissue can be compared to the amount of radioactivity of the cancer. In illustrative embodiments, the control tissue can be blood, such as aortic arch blood, liver, lung, spleen, intestine, heart, kidney, or muscle.

In illustrative embodiments, the method may comprise calculating a tumor to background ratio as a quotient of the amount of radioactivity of the cancer compared to the amount of radioactivity of the control tissue. As described herein the tumor to background ratio can be calculated using the images obtained as described herein. In illustrative examples, more than one tumor to background ratio can be calculated.

In illustrative embodiments, the tumor to background ratio can be at least about 2, 3, 4, 5, 6, 7, 8, 9, 10, 20, 30, 40, 50, 60, 70, 80, 90, 100, 150, 200, 400, 600, or 800. In additional illustrative embodiments, the tumor to background ratio can be about 2 to about 800, about 2 to about 600, about 2 to about 400, about 2 to about 200, about 2 to about 150, about 2 to about 100, about 2 to about 90, about 2 to about 80, about 2 to about 70, about 2 to about 60, about 2 to about 50, about 2 to about 40, about 2 to about 30, about 2 to about 20, about 2 to about 10, about 2 to about 9, about 2 to about 8, about 2 to about 7, about 2 to about 6, about 2 to about 5, about 2 to about 4, or about 2 to about 3. In an illustrative embodiment, the patient urinates before an image is obtained. In another illustrative embodiment, the patient has not taken a folic acid supplement within about 3 weeks of the administration of the labeled compound.

In another illustrative embodiment, relative scales may be used to quantify the intensity of uptake of the labeled compound, such as $^{99m}$Tc-etarfolatide on a tumor by tumor basis. In this embodiment, intensity of uptake may be, for example, strong if about equivalent to a control tissue (e.g., kidney), moderate if about 30% of the control tissue, or weak if about 10% of the control tissue. In this embodiment, a patient may be considered folate-receptor positive, indicating treatment with a folate-targeted drug, if the uptake is strong or moderate. In another embodiment, folate receptor positivity may first be determined in the absence of administration of the unlabeled compound, and may show that imaging using the methods described herein is indicated, if the uptake is strong or moderate.

EXAMPLES

Example 1

Unlabeled Etarfolatide and $^{99m}$Tc-Etarfolatide Administration

In FR-expressing tumor models, etarfolatide demonstrates dose-dependent saturation with a high dissociation constant (Kd=0.1 nM). Folate conjugates are rapidly taken up by high-affinity FR binding tissues (e.g., tumors, kidney) as well as by low-affinity non-FR binding tissues (e.g., intestines, choroid plexus) with low dissociation constants (Kd~1-10 μM). Clearance of $^{99m}$Tc-etarfolatide is slower from malignant binding sites than it is from non-specific binding sites as previously shown. Given the relatively short half-life of $^{99m}$Tc (~6 hours), alternative means to decrease non-specific $^{99m}$Tc-etarfolatide uptake are needed.

Through competitive FR binding, it has been shown that background uptake of $^{99m}$Tc-etarfolatide may be blocked by excess unlabeled etarfolatide (i.e., "carrier" or "cold" etarfolatide). The impact of excess folic acid or carrier etarfolatide on $^{99m}$Tc-etarfolatide tissue uptake has been evaluated in a KB tumor xenograft mouse model. When 23-30 nmol/kg $^{99m}$Tc-etarfolatide injection was co-injected with 8.5 molar excess unlabeled etarfolatide, 4-hour post injection tumor:background ratios (TBR's) were consistently higher with co-injection of unlabeled etarfolatide than with co-injection of folic acid (FIG. 1, Table 1). The vertical dotted lines in FIG. 1 represent the allometric value estimates of a 0.5 mg folic acid (the dose level currently used in clinical development), or 0.8 mg etarfolatide, mass dose.

TABLE 1

Impact of Etarfolatide or Folic Acid on Tumor:Background Ratio

| Background Tissue | Tumor:Background Ratio | |
| --- | --- | --- |
|  | Etarfolatide | Folic acid |
| Blood | 80 | 15 |
| Liver | 9 | 2 |
| Lung | 14 | 5 |
| Spleen | 65 | 15 |
| Intestine | 4 | 0.5 |
| Heart | 14 | 7 |
| Kidney | 0.5 | 0.1 |
| Muscle | 16 | 6 |

Example 2

Clinical Study—Patient Eligibility

A clinical study will be conducted to evaluate the impact of the pre-injection of unlabeled etarfolatide on $^{99m}$Tc-etarfolatide SPECT/CT images in advanced cancer patients with FR-expressing malignancies. Patients with advanced cancer and a history of ≥1 malignant lesions which are ≥15 mm on CT or MRI study or ≥20 mm on chest radiograph within 2 months of study entry may be eligible.

After eligibility confirmation, FR expression will be determined by lesion uptake of $^{99m}$Tc-etarfolatide on SPECT/CT scans from Imaging Session #1. Only participants with $^{99m}$Tc-etarfolatide uptake on ≥1 lesions measuring >15 mm on baseline SPECT/CT images, will return for the second imaging session. The study will enroll up to 18 evaluable participants. Evaluable participants are considered those who complete both imaging sessions per the protocol.

Example 3

Intra-Participant Variability in TBR on Serial SPECT/CT Imaging (Cohort 0)

Intra-patient variations with SPECT and SPECT/CT imaging have been described with registration, gray-scale normalization (i.e., altering the range of pixel intensity), and reference region choice. As significant intra-participant variability in TBR could obscure or confound the ability to detect the changes in TBR that could be attributed to the pre-injected etarfolatide, up to 6 participants (Cohort 0) will receive standard $^{99m}$Tc-etarfolatide (0.1 mg etarfolatide labeled with 20-25 mCi technetium-99m) for both imaging sessions to evaluate for intra-participant variability in TBR in 3-6 participants (Cohort 0). If intra-participant variability in TBR's is less than 25% in 3 participants, this cohort will be closed. If intra-participant variability in TBR's are ≥25% in the first 3 participants, up to 3 additional participants will be studied for further characterization of the variability. Participants may provide archived specimens (e.g., cancer tissue from biopsy or fine needle aspiration) for determination of FR status by immunohistochemical (IHC) testing.

Example 4

Background $^{99m}$Tc-Etarfolatide Uptake in Normal Tissues $^{99m}$Tc-etarfolatide uptake will be evaluated relative to several background standards (e.g. aortic arch blood pool activity, lung, and muscle) to provide radiologists with guidance for the identification of FR expressing lesions by $^{99m}$Tc-etarfolatide uptake.

Example 5

Optimal Imaging Time Point Based Upon TBR

Images taken at 1 hour post injection vs 3 hours post injection will be compared in regards to radionuclide retention and clearance in target and non-target tissues as well as TBRs to assess the effect of image timing post injection.

Example 6

The Safety and Tolerability of Sequential Injection of Up to 4 Dose Levels of Unlabeled Etarfolatide and Standard Dose $^{99m}$Tc-Etarfolatide Safety will be assessed by monitoring vital signs, including heart rate, respiratory rate, body temperature, and blood pressure, pre and post injection of $^{99m}$Tc-etarfolatide in the first imaging session and pre and post injection of unlabeled and labeled etarfolatide in the second imaging session. Baseline clinical laboratory tests will be performed at screening and pre-injection at the second imaging session. Participants will be monitored for adverse events for four days after each of the $^{99m}$Tc-etarfolatide injections.

Example 7

Study Design

A non-randomized, open-label multi-center study of sequentially injected multiple dose levels of unlabeled etarfolatide with standard dose $^{99m}$Tc-etarfolatide in advanced cancer patients will be conducted. 18 evaluable participants will be enrolled. Evaluable participants are considered those who complete both imaging session assessments per the protocol. Eligible participants will be sequentially enrolled into cohorts of 3 per the dosing schema starting with Cohort 0 (see Tables 2 and 3). Cohorts will be enrolled in a step-wise fashion. Cohort 4 may not be explored if there does not appear to be substantial differences in TBR's and image quality between cohorts 2 and 3.

In light of etarfolatide's well-defined safety profile, up to 3 participants per cohort will be enrolled simultaneously. Safety will be assessed by history, laboratory assessment prior to the etarfolatide injection, vital signs before and after the etarfolatide injection and adverse event follow up period of 4 days post last $^{99m}$Tc-etarfolatide injection. Once three participants in each cohort complete the two Imaging Sessions, a review of safety information will be completed before treatment at the next cohort begins.

TABLE 2

Calculated margins and proposed Doses

| Etarfolatide Proposed Clinical Dose in mg (mg/m²) | Rat (3.4 mg/m²) | Rabbit (4.3 mg/m²) | Mouse (1.8 mg/m²)[a] | Rabbit (5.3 mg/m²) | Mouse[b] (999 mg/m²) |
|---|---|---|---|---|---|
| 0.1 (0.06) | 57 | 72 | 30 | 88 | 16,650 |
| 0.3 (0.18) | 19 | 24 | 10 | 30 | 5,550 |
| 1.0 (0.6) | 6 | 7 | 3 | 9 | 1,665 |
| 3.0 (1.8) | 2 | 2.4 | 1 | 3 | 555 |
| 10.0 (6.0) | 0.6 | 0.7 | 0.3 | 0.9 | 167 |

[a]NOAEL (all others are NOEL)
[b]In vivo micronucleus assay - unchelated etarfolatide

TABLE 3

Etarfolatide dosing schema

| Cohort | Imaging Session #1 | Imaging Session #2 |
|---|---|---|
| 0 | 0.1 mg etarfolatide* | 0.1 mg etarfolatide* |
| 1 | 0.1 mg etarfolatide* | 0.3 mg etarfolatide + 0.1 mg etarfolatide* |
| 2 | 0.1 mg etarfolatide* | 1 mg etarfolatide + 0.1 mg etarfolatide* |
| 3 | 0.1 mg etarfolatide* | 3 mg etarfolatide + 0.1 mg etarfolatide* |
| 4 | 0.1 mg etarfolatide* | 10 mg etarfolatide + 0.1 mg etarfolatide* |

*denotes etarfolatide radiolabeled with 20-25 mCi of Technetium-99m

Imaging Session #1—

All participants enrolled in Cohort 0-4 will undergo at least 1 imaging session. During Imaging Session #1, participants will receive 0.1 mg of etarfolatide radiolabeled with 20-25 mCi of Technetium-99m (i.e., standard dose $^{99m}$Tc-etarfolatide). SPECT/CT imaging will occur approximately 1 and 3 hours post-injection. The window for the 1 hour SPECT/CT images is +0.25 hour; the window for 3 hour SPECT/CT images is −0.25 hour to +0.50 hour. FR expression will be determined by $^{99m}$Tc-etarfolatide uptake and size of the lesion(s) observed on these images.
Approximately 4-8 days (but no less than 4 days) after Imaging Session #1, participants having $^{99m}$Tc-etarfolatide uptake on ≥1 lesions measuring ≥15 mm on baseline SPECT/CT images, will return for the second imaging session.
Imaging Session #2

Approximately 4-8 days (but no less than 4 days) after Imaging Session #1, participants in Cohort 0 will receive standard dose $^{99m}$Tc-etarfolatide again, and participants in Cohorts 1-4 will first receive an injection of 1 of 4 doses of unlabeled etarfolatide followed by an injection of standard dose of $^{99m}$Tc-etarfolatide. SPECT/CT imaging will occur approximately 1 and 3 hours post injections. Participants in Cohort 0 will receive the same dose of $^{99m}$Tc-etarfolatide for both imaging sessions.

The study will enroll up to 18 evaluable participants. Evaluable participants are those who complete both imaging sessions per the protocol. Eligible participants will be sequentially enrolled into cohorts of 3 per the dosing schema starting with cohort 0 (see table above). Cohorts will be enrolled in a step-wise fashion. Cohort 4 may not be explored if there does not appear to be substantial differences in TBR's and image quality between cohorts 2 and 3. In light of $^{99m}$Tc-etarfolatide's well-defined safety profile, up to 3 participants per cohort may be enrolled simultaneously. Safety will be assessed by history, laboratory assessment prior to the etarfolatide injection, vital signs before and after etarfolatide injection and adverse event follow up period of 4 days post $^{99m}$Tc-etarfolatide injection. Once a cohort of 3 participants has completed the two Imaging Sessions, a review of safety information will be completed before dosing of the next cohort begins.

Example 8

Study Objectives

Primary Objectives:
Identify the dose of unlabeled etarfolatide followed by $^{99m}$Tc-etarfolatide, which yields the highest TBR (% injected activity) on SPECT/CT imaging.
Secondary Objectives:
1. Evaluate for intra-participant variability in TBR on serial SPECT/CT imaging (Cohort 0)
2. Explore background $^{99m}$Tc-etarfolatide uptake in various normal tissues.
3. Identify optimal imaging time point (1 hour post-injection vs 3 hour postinjection) based upon TBR.
4. Evaluate safety and tolerability of sequential injection of up to 4 dose levels of unlabeled and standard dose $^{99m}$Tc-etarfolatide.

Example 9

Patient Eligibility Criteria

Inclusion Criteria:
1. Participant must be 18 years of age or older.
2. Participant must provide informed written consent prior to enrollment.
3. Participant must have a histologically confirmed cancer (biopsy or fine needle aspiration) that is locally advanced or metastatic. Note to Investigators: Cancers with frequent FR expression are preferred but not required for study inclusion. They include (but are not limited to): endometrial cancer, non-small cell lung cancer (NSCLC), ovarian cancer, triple negative breast cancer.
4. Participant must have clinical or radiologic history of ≥1 malignant lesion measuring at ≥15 mm or CT or MRI, or ≥20 mm on chest radiograph, within 8 weeks of study entry.
5. Participant must have an Eastern Cooperative Oncology Group (ECOG) performance status of 0 or 1.
6. Participants must have adequate organ function:
   a) Bone marrow reserve: Absolute neutrophil count (ANC)≥1.5×109/L. Platelets ≥100×109/L. Hemoglobin ≥9 g/dL.

b) Hepatic: Total bilirubin ≤1.5× the upper limit of normal (ULN). Alanine aminotransferase (ALT), aspartate aminotransferase (AST)≤3.0×ULN OR ≤5.0×ULN for participants with liver metastases.
c) Renal: Serum creatinine ≤1.5×ULN, or for participants with serum creatinine >1.5 ULN, creatinine clearance ≥50 mL/min.

7. Participant of childbearing potential:
   a). All women of child bearing potential must have a negative serum pregnancy test within 1 week prior to each exposure to etarfolatide or $^{99m}$Tc-etarfolatide.
   b). Women of child bearing potential must practice an effective method of birth control (e.g., oral, transdermal or injectable contraceptives, intrauterine device [IUD], or double-barrier contraception, such as diaphragm/condom and spermicidal jelly) during their participation in the trial.
   c). Male participants who are sexually active must practice an effective method of birth control (e.g., condom and spermicidal jelly). Effective birth control methods should be used throughout study participation.

Exclusion Criteria:
1. Participant is on active cancer therapy, other than hormonal treatment.
2. Participant has known hypersensitivity to the components of the test agent or its analogs.
3. Participant is pregnant or breast-feeding.
4. Serious cardiac illness or medical conditions such as unstable angina, pulmonary embolism, or uncontrolled hypertension.
5. Participant is simultaneously participating in another investigative drug or device study. The participant must have completed the follow-up phase of any previous study at least 30 days prior to enrollment in this study.
6. Participant is currently taking folic acid supplements and cannot stop taking the supplements for a period of approximately 14-21 days (7 days prior to the first $^{99m}$Tc-etarfolatide injection and one day after the last imaging procedure).
7. Participant is currently on anti-folate therapy such as methotrexate for rheumatoid arthritis within 28 days of the first $^{99m}$Tc-etarfolatide injection.
8. Participant's physical condition is unsuitable for radionuclide imaging.
9. Participant has been administered another radiopharmaceutical within 6 months of study enrollment that would interfere with the assessment of the $^{99m}$Tc-etarfolatide images.
10. Participant is on other concurrent chemotherapy, immunotherapy, radiotherapy or investigational therapy.
11. Participant has known active hepatitis B or hepatitis C.

Example 10

Study Procedures

1. Participants should discontinue multivitamins or supplements containing folic acid at least 1 week before the first $^{99m}$Tc-etarfolatide dosing.
2. All enrolled participants will undergo a first imaging session consisting of a SPECT/CT imaging session approximately 1 and 3 hours post injection of $^{99m}$Tc-etarfolatide.
3. Participants having $^{99m}$Tc-etarfolatide uptake on ≥1 lesions measuring >15 mm on the first imaging session SPECT/CT images, will return for the second imaging session consisting of a SPECT/CT imaging session approximately 1 and 3 hours post injections of $^{99m}$Tc-etarfolatide (with or without a pre-injection of unlabeled etarfolatide, depending on cohort).

Example 11

SPECT/CT Procedures

1. Participant Instructions
   The participant should discontinue folic-acid supplements, or multivitamin supplements containing folic acid, at least one week prior to the first administration of etarfolatide.
   The participant should be instructed to drink plenty of fluids for at least 24 hours after radiopharmaceutical administration.
2. SPECT/CT Image Acquisition (at Both Imaging Time Sessions)
   Acquire co-registered SPECT/CT images approximately 1 hour and 3 post-injection.
   Ask the participant to urinate immediately before image acquisition. Place the participant in the supine position for maximum comfort.
   All participants will undergo co-registered SPECT/CT imaging of the regions of interest. This may be the chest and/or abdomen and/or pelvis depending upon the location(s) of the tumor lesions.
   For optimal imaging of the body, the arms should be elevated over the head if tolerated by the participant.
   Acquire images according to Table 4:

TABLE 4

| Imaging Parameters | |
| --- | --- |
| Camera | Dual or triple-headed detector large FOV lowenergy high-resolution (LEHR) parallel-hole collimators |
| Total projections | 120-128 |
| Matrix | 128 × 128 |
| Orbit type | Circular or elliptical |
| Orbit | 180 degrees per head with a dual detector camera or 120 degrees per head with a triple detector camera |
| Time per stop | 40 seconds |
| Total number of stops | 60 to 64 projections per head for a dual-head camera or 40 to 43 projections per head for a triple-head camera |
| Energy window | 15-20% |
| Energy keV | 140 |
| Reconstruction | Raw data must undergo tomographic reconstruction. Reconstruct data at the highest pixel resolution using iterative reconstruction (a minimum of 6 iterations is recommended) Reconstruct the SPECT into 3 orthogonal planes: transverse, sagittal, and coronal. |

3. Data Transmittal and Image Archiving
   $^{99m}$Tc-etarfolatide scan images are to be archived onto media specified by, and transmitted to, the sponsor or its designee, at intervals specified by the sponsor.
   Detailed instructions for data transmittal and image archiving will be detailed in the imaging Site Operations Manual.

Semi-Quantitative Assessment of $^{99m}$Tc-Etafolatide SPECT/CT Images

Semi-quantitative analysis will be determined by calculation of radioactivity measurement of a tumor:background ratio (TBR). Different background regions (e.g. aortic arch blood pool activity, lung or muscle) will be used to determine which background produces the optimal and reproducible TBR. Ratios will be expressed as the quotient of activity in the regions of interest (ROIs): mean counts per pixel in the tumor and mean counts in the background.

Statistical Methods

1. Quantitative Assessment of SPECT/CT Images
   Summary statistics (mean, median, standard deviation, and range) will be calculated for % ID in each region of interest at each imaging session.
   Semi-quantitative analysis will be determined by calculation of radioactivity measurement of a tumor:background ratio (TBR). Ratios will be expressed as the quotient of activity in the regions of interest (ROIs): mean counts per pixel in the tumor and mean counts in the background.
   Within participant comparisons of TBR's from Imaging Sessions #1 and #2 will be made.
   Between cohort comparisons of mean TBR's will be made.
   Between time point comparisons of mean TBR's will also be made.
2. Safety
   Participants will be assessed for adverse events for 4 days following each $^{99m}$Tc-etarfolatide injection.
   All adverse events will be listed individually and tabulated by MedDRA category.
   Summary statistics for each vital sign from baseline through post-injection.
   Summary statistics for clinical laboratory results from baseline through post-injection.

Example 12

Etarfolatide Preparation

The radiopharmaceutical diagnostic agent is composed of a folate-targeting ligand (etarfolatide) that chelates Tc-99m. The non-radioactive reagent vial (drug product) is packaged as a sterile lyophilized powder.

The radioactive drug substance will be prepared at a designated nuclear pharmacy by reconstitution with Sodium Pertechnetate Tc-99m Injection, U.S.P., as per the Nuclear Pharmacy Manual, which is expressly incorporated by reference herein.

Example 13

Etarfolatide Administration

Prior to being placed on the imaging table, the participant will be asked to empty his/her bladder. During Imaging Session #1: All participants will receive one injection of $^{99m}$Tc-etarfolatide administered via a free-flowing indwelling IV catheter. $^{99m}$Tc-etarfolatide should be administered over a period of approximately 30 seconds followed by 5-10 mL of normal saline. The injected radioactive dose should be between 20-25 mCi.

During Imaging Session #2: Participants in Cohort 0 will receive one injection of $^{99m}$Tc-etarfolatide as they did in Imaging Session #1. Participants in Cohorts 1-4 will receive two injections: an injection of unlabeled etarfolatide followed by an injection of radiolabeled etarfolatide, $^{99m}$Tc-etarfolatide. For participants in Cohorts 1-4, unlabeled etarfolatide will be administered at the cohort specified dose. The unlabeled etarfolatide should be administered via a free-flowing indwelling IV catheter.

For Cohort 1 and 2 participants, the unlabeled etarfolatide should be administered over a period of approximately 30 seconds.

For Cohort 3 participants, the unlabeled etarfolatide should be administered over a period of approximately 60 seconds.

For Cohort 4 participants, the unlabeled etarfolatide should be administered over a period of approximately 90 seconds.

Approximately 1-2 minutes after the injection of unlabeled etarfolatide, the $^{99m}$Tc-etarfolatide (radiolabeled etarfolatide) injection will be administered. $^{99m}$Tc-etarfolatide should be administered over a period of approximately 30 seconds followed by 5-10 mL of normal saline. The injected radioactive dose should be between 20-25 mCi.

Participants will be requested to provide archived specimens (e.g., cancer tissue from biopsy or fine needle aspiration) for determination of FR status by immunohistochemical (IHC) testing. Tissue donation is optional, and will not determine participant eligibility for this study.

Example 14

Nuclear Imaging

The participant should discontinue folic acid supplements for at least 1 week prior to the first administration of $^{99m}$Tc-etarfolatide. The participant should be instructed to drink plenty of fluids for at least 24 hours after radiopharmaceutical administration.

Imaging will consist of co-registered SPECT/CT imaging as detailed below at 1 hour and 3 hours post-injection of $^{99m}$Tc-etarfolatide at both imaging sessions. For SPECT/CT imaging:

All participants will undergo co-registered SPECT/CT imaging of the regions of interest. This may be of the chest and/or abdomen and/or pelvis depending on the location(s) of the tumor lesions.

For optimal co-registered SPECT/CT imaging of the body, the arms should be elevated over the head, if tolerated by the participant.

Reconstruct data at the highest pixel resolution using iterative reconstruction (a minimum of 6 iterations is recommended).

Reconstruct the SPECT into 3 orthogonal planes: transverse, sagittal, and coronal.

Acquire images according to Table 4:

Example 15

Statistical Considerations

Quantitative Assessment of SPECT/CT images Summary statistics (mean, median, standard deviation, and range) will be calculated for % ID in each region of interest at each imaging time point. Semi-quantitative analysis will be determined by calculation of radioactivity measurement of a tumor:background ratio (TBR). Ratios will be expressed as the quotient of activity in the regions of interest (ROIs): mean counts per pixel in the tumor and mean counts in the background.

Within participant comparisons of TBR's from Imaging Session #1 and Imaging Session #2 SPECT/CT images as well as between cohort comparisons of mean TBR's will be made.

Example 16

Mouse Imaging

Etarfolatide kits were used for the preparation of $^{99m}$Tc-chelated radioactive drug substance. Radiochemical purity of $^{99m}$Tc-etarfolatide was determined by HPLC attached to a radiodetector. $^{99m}$Tc-etarfolatide was investigated in vivo using mice bearing FR positive human xenograft models. Test articles were administered intravenously in mice via the lateral tail vein. $^{99m}$Tc biodistribution was determined by removing selected tissues and measuring their radioactivity content in an automatic gamma-counter. High resolution three dimensional images of the radiolabel were obtained on a dual microSPECT/CT system.

Following intravenous administration, $^{99m}$Tc-etarfolatide was rapidly captured and retained within FR-expressing tumor and kidney. Peak tissue levels occurred 1 h post injection. Tumor retention remained near maximum for approximately 18 hours, whereas $^{99m}$Tc-etarfolatide levels in normal FR-negative tissues had quickly cleared to near baseline levels after 4-8 hours. Time-based SPECT/CT imagining corroborated these tissue-based findings. While keeping the radiochemical dose constant, increasing the total etarfolatide dose was found to strikingly increase radiochemical uptake in the tumor by more than 4-fold and reaching the "summit" at a mouse dose of ~100 nmol/kg. Tumor-to-nontumor ratios consequently increased thereby improving the quality of tumor imaging. Substituting the unlabeled etarfolatide mass with folic acid did not show these effects. Importantly, tumor-to-nontumor ratios did decrease as the total etarfolatide dose was further escalated to the point where complete competitive tumor blockade was observed at 10,000 nmol/kg.

The biodistribution and SPECT/CT image quality of $^{99m}$Tc-etarfolatide may be significantly improved by i) allowing sufficient time for non-cognate tissue uptake to clear, and/or ii) administering an appropriate dose of etarfolatide. Based on these findings, both of these experimental parameters (imaging time and etarfolatide dose) are currently being tested at the clinical level in cancer patients.

What is claimed is:

1. A method of imaging a cancer, the method comprising administering to a patient an unlabeled compound according to Formula I

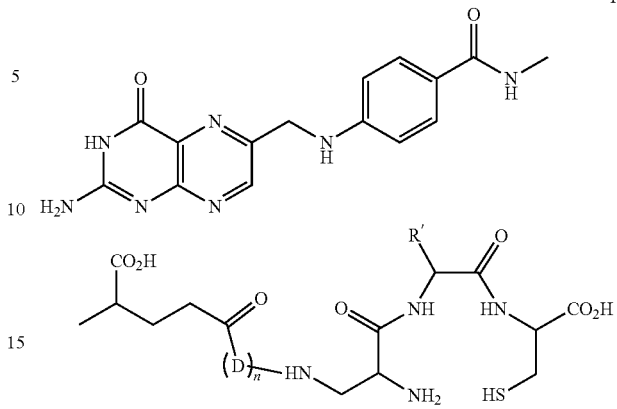

or a pharmaceutically acceptable salt thereof, wherein R' is hydrogen, or R' is selected from the group consisting of alkyl, aminoalkyl, carboxyalkyl, hydroxyalkyl, heteroalkyl, aryl, arylalkyl and heteroarylalkyl, each of which is optionally substituted, wherein D is a divalent linker, and wherein n is 0 or 1, and administering to the patient a labeled compound according to Formula II

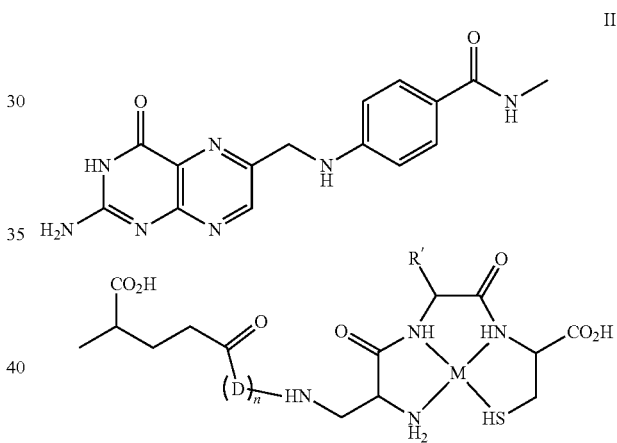

or a pharmaceutically acceptable salt thereof, wherein R' is hydrogen, or R' is selected from the group consisting of alkyl, aminoalkyl, carboxyalkyl, hydroxyalkyl, heteroalkyl, aryl, arylalkyl and heteroarylalkyl, each of which is optionally substituted, wherein D is a divalent linker, wherein n is 0 or 1, and wherein M is a cation of a radionuclide.

2. The method of claim 1, wherein the unlabeled compound is of the formula

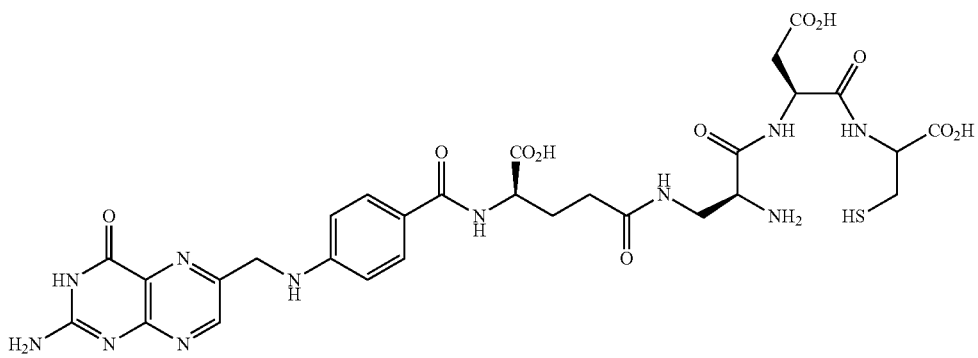 [SMILES: Nc1nc2ncc(CNc3ccc(C(=O)N[C@H](CCC(=O)NC[C@H](N)C(=O)N[C@@H](CC(=O)O)C(=O)NC(CS)C(=O)O)C(=O)O)cc3)nc2c(=O)[nH]1]

or a pharmaceutically acceptable salt thereof, and the labeled compound is of the formula

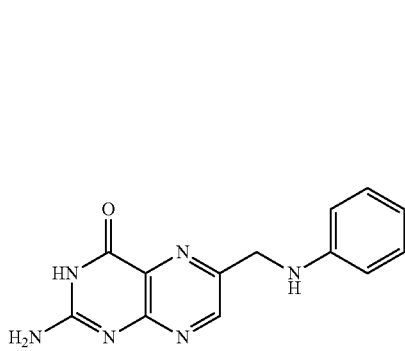 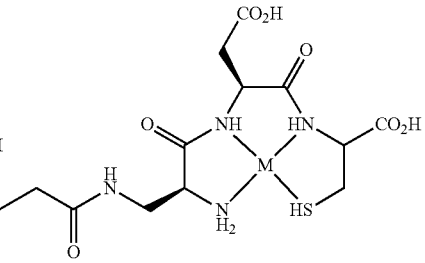

or a pharmaceutically acceptable salt thereof, and wherein M is a cation of a radionuclide.

3. The method of claim 1, wherein the patient is administered the unlabeled compound, or a pharmaceutically acceptable salt thereof, before the patient is administered the labeled compound, or a pharmaceutically acceptable salt thereof.

4. The method of claim 1, wherein the cancer is selected from the group consisting of lung cancer, bone cancer, pancreatic cancer, skin cancer, cancer of the head, cancer of the neck, cutaneous melanoma, intraocular melanoma uterine cancer, ovarian cancer, endometrial cancer, rectal cancer, stomach cancer, colon cancer, breast cancer, triple negative breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, non-small cell lung cancer, cancer of the adrenal gland, sarcoma of soft tissue, cancer of the urethra, prostate cancer, chronic leukemia, acute leukemia, lymphocytic lymphoma, pleural mesothelioma, cancer of the bladder, Burkitt's lymphoma, cancer of the ureter, cancer of the kidney, renal cell carcinoma, carcinoma of the renal pelvis, neoplasms of the central nervous system (CNS), primary CNS lymphoma, spinal axis tumors, brain stem glioma, pituitary adenoma, and adenocarcinoma of the gastroesophageal junction.

5. The method of claim 1, wherein the cancer is a folate receptor expressing cancer.

6. The method of claim 1, wherein the radionuclide is selected from the group consisting of an isotope of gallium, an isotope of indium, an isotope of copper, an isotope of technetium, and an isotope of rhenium.

7. The method of claim 1, wherein the cancer is imaged about 0.5 hours to about 8 hours after administration of the labeled compound, or a pharmaceutically acceptable salt thereof.

8. The method of claim 1, wherein the patient is administered about a 2-fold to about a 1000-fold excess of the unlabeled compound, or a pharmaceutically acceptable salt thereof, relative to the labeled compound, or pharmaceutically acceptable salt thereof.

9. The method of claim 1, wherein the patient is administered about 0.1 mg to about 20 mg of the unlabeled compound, or a pharmaceutically acceptable salt thereof, and the patient is administered about 0.01 mg to about 2 mg of the labeled compound, or a pharmaceutically acceptable salt thereof.

10. The method of claim 1, wherein the patient is administered a mass dose of about 50 nmol/kg to about 3000 nmol/kg of patient body weight of the unlabeled compound, or a pharmaceutically acceptable salt thereof, and the labeled compound, or a pharmaceutically acceptable salt thereof.

11. The method of claim 1, wherein the patient is administered the unlabeled compound or a pharmaceutically acceptable salt thereof, over a period of about 15 seconds to about 2 minutes.

12. The method of claim 1, wherein the patient is administered saline after the patient is administered the labeled compound, or a pharmaceutically acceptable salt thereof.

13. The method of claim 1, wherein the cancer is imaged by PET imaging.

14. The method of claim 1, wherein the cancer is imaged by MRI imaging.

15. The method of claim 1, wherein the cancer is imaged by SPECT/CT imaging.

16. The method of claim 1, further comprising the step of measuring an amount of radioactivity of the cancer and an amount of radioactivity of a control tissue.

17. The method claim 16 wherein the control tissue is selected from the group consisting of blood, liver, lung, spleen, intestine, heart, kidney, and muscle.

18. The method of claim 16, further comprising the step of calculating a tumor to background ratio as a quotient of the amount of radioactivity of the cancer compared to the amount of radioactivity of the control tissue.

19. The method of claim 1, wherein the labeled compound comprises about 20 mCi to about 25 mCi of technetium-99m.

20. The method of claim 1, wherein multiple doses of the unlabeled compound, or a pharmaceutically acceptable salt thereof, and the labeled compound, or a pharmaceutically acceptable salt thereof, are administered.

21. The method of claim 1, wherein the labeled compound, or a pharmaceutically acceptable salt thereof, is administered to the patient, the unlabeled compound, or a pharmaceutically acceptable salt thereof, is then administered to the patient, and the labeled compound, or a pharmaceutically acceptable salt thereof, is administered to the patient a second time after the unlabeled compound, or a pharmaceutically acceptable salt thereof, is administered to the patient.

22. The method of claim 21 wherein the labeled compound, or a pharmaceutically acceptable salt thereof, is first administered to the patient on day 1 and the unlabeled compound, or a pharmaceutically acceptable salt thereof, and the labeled compound, or a pharmaceutically acceptable salt thereof, are then administered to the patient on day 4 to day 10.

23. The method of claim 21, wherein the patient is administered about 0.3 mg to about 10 mg of the unlabeled compound, or a pharmaceutically acceptable salt thereof, and the patient is administered about 0.05 mg to about 0.5 mg of the labeled compound, or a pharmaceutically acceptable salt thereof, each time the labeled compound, or a pharmaceutically acceptable salt thereof, is administered to the patient.

24. The method of claim 21, wherein the patient is imaged after each administration of the labeled compound, or a pharmaceutically acceptable salt thereof.

* * * * *